(12) United States Patent
Lakshman

(10) Patent No.: US 9,040,498 B2
(45) Date of Patent: May 26, 2015

(54) 1,2,3-TRIAZOLYL PURINE DERIVATIVES

(71) Applicant: RESEARCH FOUNDATION OF THE CITY UNIVERSITY OF NEW YORK, New York, NY (US)

(72) Inventor: Mahesh K. Lakshman, Teaneck, NJ (US)

(73) Assignee: Research Foundation of the City University of New York, New York, NY (US)

( * ) Notice: Subject to any disclaimer, the term of this patent is extended or adjusted under 35 U.S.C. 154(b) by 9 days.

(21) Appl. No.: 13/936,770

(22) Filed: Jul. 8, 2013

(65) Prior Publication Data

US 2014/0011763 A1 Jan. 9, 2014

Related U.S. Application Data

(60) Provisional application No. 61/668,879, filed on Jul. 6, 2012.

(51) Int. Cl.
| | |
|---|---|
| *A01N 43/04* | (2006.01) |
| *A61K 31/70* | (2006.01) |
| *C07H 23/00* | (2006.01) |
| *C07H 19/16* | (2006.01) |
| *C07H 19/167* | (2006.01) |
| *C07H 19/173* | (2006.01) |

(52) U.S. Cl.
CPC ............... *C07H 23/00* (2013.01); *C07H 19/16* (2013.01); *C07H 19/167* (2013.01); *C07H 19/173* (2013.01)

(58) Field of Classification Search
None
See application file for complete search history.

(56) References Cited

FOREIGN PATENT DOCUMENTS

CA 2609051 11/2006

OTHER PUBLICATIONS

Lakshman et al. J. Org. Chem. (2012), vol. 77, pp. 5870-5883.*
Lakshman, Mahesh K., et al., "Synthesis and Biological Properties of C-2 Triazolylinosine Derivatives", J. Org. Chem 2012, 77, pp. 5870-5883.

* cited by examiner

*Primary Examiner* — Patrick Lewis
(74) *Attorney, Agent, or Firm* — Hoffmann & Baron, LLP

(57) ABSTRACT

The present invention relates to novel 1,2,3-triazolyl purine derivatives. The invention also relates to using the derivatives to treat cancer and various viral infections. An example of a 1,2,3-triazolyl purine derivative of the invention is 35 Claims, No Drawings

1,2,3-TRIAZOLYL PURINE DERIVATIVES

CROSS-REFERENCE TO RELATED APPLICATION

This application claims priority from U.S. Provisional Application Ser. No. 61/668,879, filed on Jul. 6, 2012, which is incorporated herein by reference.

This invention was supported, in part, by the National Institutes of Health/National Institute of Allergy and Infectious Diseases, grant number 1R21 AI094545-01. The United States government has rights in the invention.

BACKGROUND OF THE INVENTION

The Cu-catalyzed version of the classic Huisgen azide-alkyne cycloaddition is a highly atom-economical reaction, often requiring mild conditions. Both factors render Cu-catalyzed azide-alkyne cycloaddition (CuAAC) highly attractive for the modification of complex and sensitive molecules such as nucleosides. Thus, such a method can be readily applied for the modification of nucleosides. Nucleosides are a highly important class of biomolecules, with applications in biochemistry, biology, as biological probes, and in medicine. $O^6$-protected 2-azidoinosine derivatives and their 2'-deoxyinosine analogues are potentially very useful intermediates for use in CuAAC reactions. C-2 (1,2,3-triazol-1H-yl)inosine and 2'-deoxyinosine analogues can be synthesized by $O^6$-benzotriazolyl derivatives, and these can be further converted to C-2 (1,2,3-triazol-1H-yl)adenosine analogues. Both classes of compounds are anticipated to have high importance in the fields of biochemistry, biology, and medicine.

SUMMARY OF THE INVENTION

In one embodiment, the invention relates to a compound having Formula I,

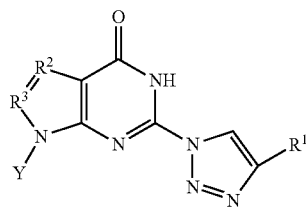

Formula I wherein:
$R^1$ represents an alkyl, an aryl, —$SiR^4$, —$SnR^5$, —$B(R^4)_2$, —$B(OH)_2$, an amide, an imide, or an organometallic;
$R^2$ and $R^3$ independently represent N, CH, or $CR^6$;
$R^4$ independently represents —$R^5$ or —$OR^5$;
$R^5$, $R^7$ and $R^8$, independently of each other and independently at each position, represent alkyl, cycloalkyl, or aryl;
$R^7$ and $R^8$ independently, may be combined to represent a heterocyclic alkyl or a heterocyclic aryl;
$R^6$ independently represents an alkyl or an aryl;
Y represents H, an alkyl, an aryl, or a saccharide moiety;
alkyl groups are branched or unbranched, saturated or unsaturated, and have 1-18 carbon atoms in their longest chain;
cycloalkyl groups are carbocyclic or heterocyclic, fused or unfused, non-aromatic ring systems having a total of 5-16 ring members including substituent rings;
aryl groups are carbocyclic or heterocyclic;
carbocyclic aryl groups are fused or unfused ring systems having a total of 6-16 ring members including substituent rings;
heterocyclic aryl groups are fused or unfused ring systems having a total of 5-16 ring members including substituent rings;
halo substituents are fluoro, chloro, bromo, or iodo;
each alkyl, cycloalkyl, and aryl, independently, may be unsubstituted or substituted with one or more substituent at any position;
alkyl substituents are halo, hydroxyl, —$OR^5$, —$SR^5$, —$S(O)R^4$, —$S(O)_2R^4$, —$NH_2$, —$NHR^5$, —$NR^7R^8$, cycloalkyl, or aryl;
cycloalkyl substituents are halo, hydroxyl, —$OR^5$, —$SR^5$, —$NH_2$, —$NHR^5$, —$NR^7R^8$, alkyl, cycloalkyl, or aryl;
aryl substituents are halo, hydroxyl, —$OR^5$, —$SR^5$, —$NH_2$, —$NHR^5$, —$NR^7R^8$, —CN, alkyl, cycloalkyl, aryl, nitro, or carboxyl; and
heterocyclic alkyl and heterocyclic aryl have at least one heteroatom selected from the group consisting of oxygen, nitrogen and sulfur.

In another embodiment, the invention relates to a compound having Formula II,

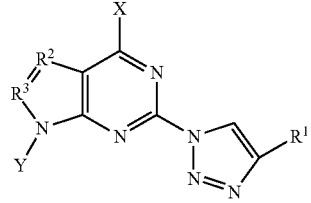

Formula II wherein:
$R^1$ represents an alkyl, an aryl, —$SiR^4$, —$SnR^5$, —$B(R^4)_2$, —$B(OH)_2$, an amide, an imide, or an organometallic;
$R^2$ and $R^3$ independently represent N, CH, or $CR^6$;
X represents —$OR^9$, —$SR^9$, or —$NR^9R^{10}$;
Y represents H, an alkyl, an aryl, or a saccharide moiety;
$R^4$ independently represents —$R^5$ or —$OR^5$;
$R^5$, $R^7$ and $R^8$, independently of each other and independently at each position, represent alkyl, cycloalkyl, or aryl; and
$R^6$ independently represents an alkyl or an aryl;
$R^9$ and $R^{10}$ independently represent H, an alkyl, or an aryl;
$R^7$ and $R^8$, $R^9$ and $R^{10}$ independently, may be combined to represent a heterocyclic alkyl or a heterocyclic aryl;
alkyl groups are branched or unbranched, saturated or unsaturated, and have 1-18 carbon atoms in their longest chain;
cycloalkyl groups are carbocyclic or heterocyclic, fused or unfused, non-aromatic ring systems having a total of 5-16 ring members including substituent rings;
aryl groups are carbocyclic or heterocyclic;
carbocyclic aryl groups are fused or unfused ring systems having a total of 6-16 ring members including substituent rings;
heterocyclic aryl groups are fused or unfused ring systems having a total of 5-16 ring members including substituent rings;
halo substituents are fluoro, chloro, bromo, or iodo;
each alkyl, cycloalkyl, and aryl, independently, may be unsubstituted or substituted with one or more substituent at any position;
alkyl substituents are halo, hydroxyl, —$OR^5$, —$SR^5$, —$S(O)R^4$, —$S(O)_2R^4$, —$NH_2$, —$NHR^5$, —$NR^7R^8$, cycloalkyl, or aryl;

cycloalkyl substituents are halo, hydroxyl, —OR$^5$, —SR$^5$, —NH$_2$, —NHR$^5$, —NR$^7$R$^8$, alkyl, cycloalkyl, or aryl;
aryl substituents are halo, hydroxyl, —OR$^5$, —SR$^5$, —NH$_2$, —NHR$^5$, —NR$^7$R$^8$, —CN, alkyl, cycloalkyl, aryl, nitro, or carboxyl; and
heterocyclic alkyl and heterocyclic aryl have at least one heteroatom selected from the group consisting of oxygen, nitrogen and sulfur.

In another embodiment, the invention relates to a compound having Formula III,

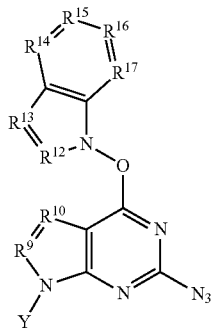

Formula III wherein:
R$^9$, R$^{10}$, R$^{12}$, R$^{13}$, R$^{14}$, R$^{15}$, R$^{16}$, and R$^{17}$ independently represent N or CR$^{11}$;
R$^{11}$ independently represents —R$^{18}$, —OR$^{19}$, —SR$^{19}$, —N(R$^{18}$)$_2$, R$^{18}$C(O)—, nitro, or halo;
R$^{18}$ independently represents H, an alkyl group, or an aryl;
R$^{19}$ independently represents R$^{18}$ or a protecting group;
Y represents R$^{18}$ or a saccharide moiety;
alkyl groups are branched or unbranched, saturated or unsaturated, and have 1-18 carbon atoms in their longest chain;
cycloalkyl groups are carbocyclic or heterocyclic, fused or unfused, non-aromatic ring systems having a total of 5-16 ring members including substituent rings;
aryl groups are carbocyclic or heterocyclic;
carbocyclic aryl groups are fused or unfused ring systems having a total of 6-16 ring members including substituent rings;
heterocyclic aryl groups are fused or unfused ring systems having a total of 5-16 ring members including substituent rings;
halo substituents are fluoro, chloro, bromo, or iodo;
each alkyl, cycloalkyl, and aryl, independently, may be unsubstituted or substituted with one or more substituent at any position;
alkyl substituents are halo, hydroxyl, —OR$^5$, —SR$^5$, —S(O)R$^4$, —S(O)$_2$R$^4$, —NH$_2$, —NHR$^5$, —NR$^7$R$^8$, cycloalkyl, or aryl; cycloalkyl substituents are halo, hydroxyl, —OR$^5$, —SR$^5$, —NH$_2$, —NHR$^5$, —NR$^7$R$^8$, alkyl, cycloalkyl, or aryl;
aryl substituents are halo, hydroxyl, —OR$^5$, —SR$^5$, —NH$_2$, —NHR$^5$, —NR$^7$R$^8$, —CN, alkyl, cycloalkyl, aryl, nitro, or carboxyl; and
heterocyclic alkyl and heterocyclic aryl have at least one heteroatom selected from the group consisting of oxygen, nitrogen and sulfur.
R$^4$ independently represents —R$^5$ or —OR$^5$;
R$^5$, R$^7$ and R$^8$, independently of each other and independently at each position, represent alkyl, cycloalkyl, or aryl; and
R$^7$ and R$^8$ independently, may be combined to represent a heterocyclic alkyl or a heterocyclic aryl.

In another embodiment, the invention relates to a method of treating cancer, comprising administering to a patient in need thereof an effective amount of a compound of Formula I or a compound below:

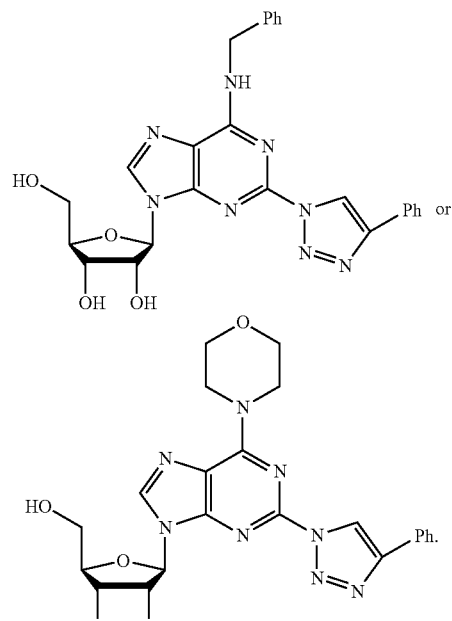

DETAILED DESCRIPTION

The invention relates to 1,2,3-triazolylpurine derivatives synthesized by CuAAC reactions that may possess anticancer and antiviral properties.

In one embodiment, the invention relates to a compound having Formula I,

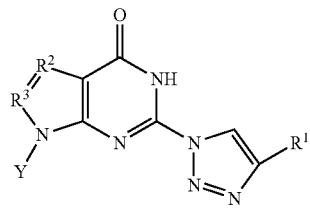

Formula I

In Formula I, R$^1$ represents an alkyl, an aryl, —SiR$^4$, —SnR$^5$, —B(R$^4$)$_2$, —B(OH)$_2$, an amide, an imide, or an organometallic. R$^1$ is preferably phenyl. Alkyls, aryls, amides, imides, and organometallics are described below.

R$^2$ and R$^3$ independently represent N, CH, or CR$^6$. For example, R$^2$ may represent CR$^6$ and R$^3$ may represent CH. In a preferred embodiment, R$^2$ is N and R$^3$ is CH.

R$^4$ independently represents —R$^5$ or —OR$^5$. For example, if R$^1$ represents —B(R$^4$)$_2$, then R$^4$ may represent both —R$^5$ and —OR$^5$, and R$^1$ would represent B(R$^5$)(OR$^5$).

R$^5$ represents alkyl, cycloalkyl, or aryl. Cycloalkyl groups are described below.

R$^6$ independently represents an alkyl or an aryl. Therefore, if R$^2$ is CR$^6$ and R$^3$ is CR$^6$, then R$^2$ may represent C(alkyl) and R$^3$ may represent C(aryl).

Y represents H, an alkyl, an aryl, or a saccharide moiety. Saccharide moieties are described below.

Alkyl groups are branched or unbranched, saturated or unsaturated, and have 1-18 carbon atoms in their longest chain. Some examples of suitable straight-chained, saturated alkyl groups include methyl, ethyl, n-propyl, n-butyl, n-pentyl, n-hexyl groups and dodecyl and hexadecyl. Preferred straight chain, saturated alkyl groups include methyl and ethyl.

Some examples of suitable branched, saturated alkyl groups include iso-propyl, iso-butyl, sec-butyl, t-butyl, 1-methylbutyl, 2-methylbutyl, 3-methylbutyl(isopentyl), 1,1-dimethylpropyl, 1,2-dimethylpropyl, 2,2-dimethylpropyl(neopentyl), 1-methylpentyl, 2-methylpentyl, 3-methylpentyl, 4-methylpentyl groups, and 2-methyl-5-ethyldecyl. Preferred branched, saturated alkyl groups include isopropyl and t-butyl.

Some examples of unsaturated alkyl groups include ethenyl, ethynyl, propenyl, propargyl, isopropenyl, crotyl, 1-hexenyl, and 1-octenyl.

Cycloalkyl groups are carbocyclic or heterocyclic, fused or unfused, non-aromatic ring systems having a total of 5-16 ring members including substituent rings. Ring systems are monocyclic, bicyclic, tricyclic, or tetracyclic and can be bridged or non-bridged.

Some examples of carbocyclic alkyl groups include cyclobutanyl, cyclopentanyl, cyclohexanyl, and cycloheptanyl. Examples of fused carbocyclic alkyl groups include indenyl, isoindenyl. Bridged groups include bicyclo [2.2.1]heptane, bicycico [5.2.0]nonane, and bicyclo [5.2.0]nonane.

Some examples of heterocyclic alkyl groups include pyrrolidinyl, piperidinyl, piperazinyl, tetrahydrofuranyl, morpholino, and oxazolidinyl. Examples of fused heterocyclic alkyl groups include benzomorpholino, benzopyrrolidinyl, indolinyl, and benzopiperidinyl.

Aryl groups can be either carbocyclic or heterocyclic.

Carbocyclic aryl groups are fused or unfused ring systems having a total of 6-16 ring members including substituent rings. A preferred unfused carbocyclic aryl group is phenyl. Some examples of fused carbocyclic aryl groups include naphthyl, phenanthryl, anthracenyl, triphenylenyl, chrysenyl, and pyrenyl.

Heterocyclic aryl groups are fused or unfused ring systems having a total of 5-16 ring members including substituent rings.

Some examples of unfused heterocyclic aryl groups include thienyl, furyl, pyrrolyl, pyrazolyl, imidazolyl, oxazolyl, thiazolyl, pyridinyl, pyridazinyl, pyrimidinyl, and pyrazinyl. Some examples of fused heterocyclic aryl groups include purinyl, 1,4-diazanaphthalenyl, indolyl, benzimidazolyl, 4,5-diazaphenanthrenyl, benzoxazolyl, isoindolyl, quinolinyl, isoquinolinyl, and benzofuranyl.

Halo substituents are fluoro, chloro, bromo, or iodo. Preferred halo substituents are fluoro, chloro, or bromo.

Each alkyl, cycloalkyl, and aryl, independently, may be unsubstituted or substituted with one or more substituent at any position. Alkyl substituents are halo, hydroxyl, —OR$^5$, —SR$^5$, —S(O)R$^4$, —S(O)$_2$R$^4$, —NH$_2$, —NHR$^5$, —NR$^7$R$^8$, cycloalkyl, and aryl. Cycloalkyl substituents are halo, hydroxyl, —OR$^5$, —SR$^5$, —NH$_2$, —NHR$^5$, —NR$^7$R$^8$, alkyl, cycloalkyl, and aryl. Aryl substituents are halo, hydroxyl, —OR$^5$, —SR$^5$, —NH$_2$, —NHR$^5$, —NR$^7$R$^8$, —CN, alkyl, cycloalkyl, aryl, nitro, and carboxyl.

Heterocyclic alkyl and heterocyclic aryl groups have at least one heteroatom selected from oxygen, nitrogen, and sulfur.

$R^7$ and $R^8$, independently of each other and independently at each position, represent alkyl, cycloalkyl, or aryl. $R^7$ and $R^8$ independently, may be combined to represent a heterocyclic alkyl or a heterocyclic aryl.

For example, if $R^1$ is methyl substituted with —NR$^7$R$^8$, then $R^7$ and $R^8$ can be combined to represent a heterocyclic aryl ring, resulting in the following structure:

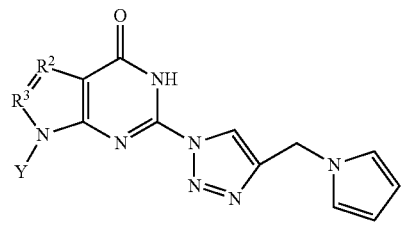

An imide is a functional group consisting of two acyl groups bound to a nitrogen atom. When $R^1$ is an imide, the imide can be bound to the $R^1$ position of the triazolyl at any possible position on the imide.

In a preferred embodiment, the imide may be represented by:

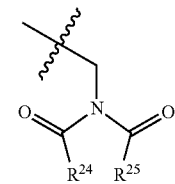

$R^{24}$ and $R^{25}$ are independently an alkyl or an aryl. $R^{24}$ and $R^{25}$ independently, may be combined to represent a succinimidyl group that may be fused or unfused, and substituted or unsubstituted. An unfused succinimidyl group is shown below:

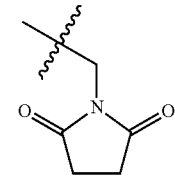 [SMILES: *CN1C(=O)CCC1=O]

A preferred fused succinimidyl group is the phthalimidyl group shown below:

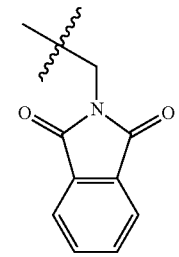 [SMILES: *CN1C(=O)c2ccccc2C1=O]

An amide is a functional group that includes an organic amide, a sulfonamide, and a phosphoramide. Preferred amides include organic amides. When $R^1$ is an amide, the amide can be bound to the $R^1$ position of the triazolyl at any possible position on the amide.

In a preferred embodiment, the amide is bound to the triazolyl at the N-position of the amide. For example, the amide may be represented by:

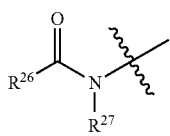

$R^{26}$ and $R^{27}$ are independently an alkyl or an aryl.

Organometallic moieties preferably contain the following transition metals: Fe, Mo, Ru, or Pt. A preferred organometallic moiety is ferrocenyl. Other organometallic moieties similar to ferrocenyl are also preferred.

Saccharide moieties that can be used in this invention can be any monosaccharide or polysaccharide. Preferred polysaccharides include disaccharides and trisaccharides. The maximum number of saccharides in a polysaccharide is typically ten, preferably five. The saccharides can be in either the D or L configuration. Monosaccharides can be either aldoses or ketoses. The number of carbons of the saccharide can be from three carbons to about six carbons. An example of a three-carbon sugar is glyceraldehyde. Examples of four carbon sugars include erythrose and threose. Examples of five carbon sugars include ribose, arabinose, xylose, and lyxose. Examples of six carbon sugars include allose, altrose, glucose, mannose, gulose, idose, galactose, and talose. Saccharides further include the corresponding deoxy derivatives.

In a particular embodiment of the invention, the saccharide has the following structure:

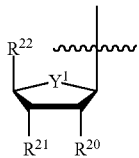

$Y^1$ represents C, N, or O. $Y^1$ is preferably O.

$R^{20}$ and $R^{21}$ independently represent H, —$OR^{23}$, —$NR^7R^8$, $R^6$, or halo.

$R^{22}$ represents H, OH, —$CH_2OR^6$, —$CH_2OR^{23}$, —$NR^7R^8$, —$CH_2NR^7R^8$, $R^6$, or halo. Preferably, $R^{22}$ represents H, —OH, —$CH_2OR^6$, —$CH_2OR^{23}$, —$NR^7R^8$, —$CH_2NR^7R^8$, or $R^6$. Most preferably, $R^{22}$ represents —$CH_2O(alkyl)$ or —$CH_2OR^{23}$.

$R^{23}$ represents H or a protecting group.

Preferably, the saccharide is a 1-ribosyl or 2'-deoxy-1-ribosyl moiety.

In this specification, protecting groups can be essentially any group suitable for the protection of a hydroxyl group, as known in the art. The phrase "protecting group" indicates any functionality that is used to replace a hydrogen atom on an alcohol, and which can easily be removed with restoration of the hydrogen without altering the structure of the remainder of the molecule.

Protecting groups are reviewed in *Protecting groups* by Kocienski, Philip J. Stuttgart, N.Y., Georg Thieme, 2005; and in *Protective groups in organic synthesis* by Greene, Theodora W. and Wuts, Peter G. M. New York, Wiley, 1999. Some examples are given below, but are not meant to be inclusive.

Useful protecting groups for compounds of the invention include, but are not limited to, the ester class and the acetal/ketal class. The ester class of protecting groups is well known in the art for protecting hydroxyl groups.

The acetal/ketal class of protecting groups can be represented according to the formula: —$C(OR^{30})(R^{31})(R^{32})$. $R^{30}$ is preferably an alkyl group, $R^{31}$ is preferably an alkyl group, an aryl group, or a hydrogen atom, and $R^{32}$ is preferably an alkyl group or a hydrogen atom. The alkyl groups of $R^{30}$, $R^{31}$, and $R^{32}$ may be any of those described above, and preferably have one to four carbon atoms, typically methyl or ethyl. The alkyl groups of $R^{30}$ and $R^{31}$ may also be joined to form a five- or six-membered saturated ring. The aryl group of $R^{31}$ may be any carbocyclic or heterocyclic aryl group described above, and is preferably phenyl, pyridinyl, pyrrolyl, or furanyl. Some preferred acetal/ketal protecting groups include methoxymethyl, ethoxymethyl, tetrahydropyranyl, and benzyloxymethyl.

Another example of a class of suitable protecting groups for $R^{23}$ includes the class of silyl protecting groups. The class of silyl protecting groups can be represented according to the formula: —$Si(OR^{33})(O_yR^{34})(O_zR^{35})$.

In the formula above for silyl protecting groups, $R^{33}$, $R^{34}$, and $R^{35}$ each independently represents any of the alkyl groups or carbocyclic or heterocyclic aryl groups described above. The subscripts x, y, and z independently represent 0 or 1. When x, y, or z is 0, then the oxygen atom to which the subscript is associated is absent. When x, y, or z is 1, then the oxygen atom to which the subscript is associated, is present.

Some examples of silyl protecting groups wherein x, y, and z are all 0, include triethylsilyl, tri-(n-propyl)silyl, triisopropylsilyl, tri-(n-butyl)silyl, triisobutylsilyl, t-butyldimethylsilyl, t-butyldiphenylsilyl, phenyldimethylsilyl, methyldiphenylsilyl, and triphenylsilyl. Some examples of silyl protecting groups wherein at least one of x, y, and z is 1, include trimethoxysilyl, dimethoxymethylsilyl, methoxydimethylsilyl, trifluoromethoxymethylsilyl, ethoxydimethylsilyl, methoxydiethylsilyl, isopropoxydimethylsilyl, phenoxydimethylsilyl, phenoxydiethylsilyl, methyldiphenoxysilyl, [2,4,6-tri-(t-butyl)phenoxy]dimethylsilyl, t-butoxydimethylsilyl, t-butoxydiphenylsilyl, t-butylmethoxyphenylsilyl, and methoxydiphenylsilyl.

Another example of a class of suitable protecting groups includes arylmethyl protecting groups, which protect a hydroxyl group by converting it to an arylmethyl ether. The aryl group may be any of the carbocyclic or heterocyclic aryl groups described above. Some examples of preferred aryl groups include phenyl, pyridinyl, pyrrolyl, or furanyl, optionally substituted with methoxy, ethoxy, nitro, or halo. Some preferred members of this class of protecting groups include benzyl, p-methoxybenzyl, and p-ethoxybenzyl.

Trityl ethers are another class of suitable protecting group. Some examples of trityl ethers include monomethoxy trityl ether, dimethoxytrityl ether, and trimethoxy trityl ether.

In another embodiment, the invention relates to a compound having Formula II,

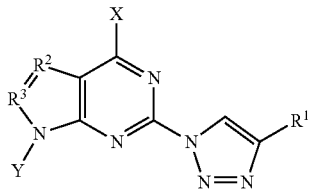

Formula II

In Formula II, $R^1$, $R^2$, $R^3$, and Y are as described above.

X represents —$OR^9$, —$SR^9$, or —$NR^9R^{10}$. Preferably, X is —$NR^9R^{10}$.

$R^9$ and $R^{10}$ independently represent H, an alkyl, or an aryl. $R^9$ and $R^{10}$ may be combined to represent a heterocyclic alkyl or a heterocyclic aryl. Preferably, $R^9$ and $R^{10}$ represent H and $CH_2Ph$, respectively. In another preferred embodiment, $R^9$ and $R^{10}$ are combined to represent $CH_2CH_2OCH_2CH_2$, therefore X is morpholinyl.

In a preferred embodiment of Formula II, X is —$NR^9R^{10}$ and $R^1$ represents —$SiR^4$, —$SnR^5$, —$B(R^4)_2$, —$B(OH)_2$, an imide, or an organometallic. In another preferred embodiment of Formula II, X is —$NR^9R^{10}$ and $R^9$ and $R^{10}$ independently represent an alkyl or an aryl.

In another embodiment, the invention relates to a compound having Formula III,

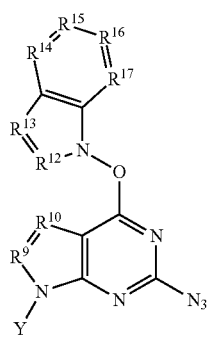

Formula III

In Formula III, $R^9$, $R^{10}$, $R^{12}$, $R^{13}$, $R^{14}$, $R^{15}$, $R^{16}$, and $R^{17}$ independently represent N or $CR^{11}$. Preferably, no more than one of $R^{14}$, $R^{15}$, $R^{16}$, and $R^{17}$ represent N. Most preferably, $R^9$, $R^{14}$, $R^{15}$, $R^{16}$, and $CR^{11}$; $R^{10}$, $R^{12}$, and $R^{13}$ are N; and $R^{17}$ is N or $CR^{11}$.

$R^{11}$ independently represents —$R^{18}$, —$OR^{19}$, —$SR^{19}$, —$N(R^{18})_2$, $R^{18}C(O)$—, nitro, or halo.

$R^{18}$ independently represents H, an alkyl group, or an aryl. $R^{11}$ and $R^{18}$ are preferably H.

$R^{19}$ independently represents $R^{18}$ or a protecting group.

Y is as described above.

In this specification, groups of various parameters containing multiple members are described. Within a group of parameters, each member may be combined with any one or more of the other members to make additional sub-groups. For example, if the members of a group are a, b, c, d, and e, additional sub-groups specifically contemplated include any two, three, or four of the members, e.g., a and c; a, d, and e; b, c, d, and e; etc.

In some cases, the members of a first group of parameters, e.g., a, b, c, d, and e, may be combined with the members of a second group of parameters, e.g., A, B, C, D, and E. Any member of the first group or of a sub-group thereof may be combined with any member of the second group or of a sub-group thereof to form additional groups, i.e., b with C; a and c with B, D, and E, etc.

For example, in the present invention, groups of various parameters are defined (e.g. $R^1$, $R^2$, $R^3$, $R^4$, $R^5$, $R^6$, $R^{18}$, Y, and $Y^1$). Each group contains multiple members. For example, $R^{18}$ represents H, an alkyl, or an aryl. Each member may be combined with each other member to form additional sub-groups, e.g., H and alkyl, H and aryl, and alkyl and aryl.

The instant invention further contemplates embodiments in which each element listed under one group may be combined with each and every element listed under any other group. For example, $R^1$ represents an alkyl, an aryl, —$SiR^4$, —$SnR^5$, —$B(R^4)_2$, —$B(OH)_2$, an amide, an imide, or an organometallic. $R^2$ and $R^3$ are defined above as independently representing N, CH, or $CR^6$. Each element of $R^1$ (an alkyl, an aryl, —$SiR^4$, —$SnR^5$, —$B(R^4)_2$, —$B(OH)_2$, an amide, an imide, or an organometallic) can be combined with each and every element of $R^2$ and $R^3$ (N, CH, or $CR^6$). For example, in one embodiment, $R^1$ may be methyl, $R^2$ may be CH, and $R^3$ may be $CR^6$. Alternatively, $R^1$ may be —$SiR^4$, $R^2$ may be N, and $R^3$ may be N, etc. Similarly, a third group is Y, in which the elements are defined as Y represents H, an alkyl, an aryl, or a saccharide moiety. Each of the above embodiments may be combined with each and every element of Y. For example, in the embodiment wherein $R^1$ is —$B(R^4)_2$, $R^2$ is N, and $R^3$ is $CR^6$, Y may be a saccharide moiety (or any other chemical moiety within the element of Y).

With each group, it is specifically contemplated that any one or more members can be excluded. For example, if $R^1$ is defined as an alkyl, an aryl, —$SiR^4$, —$SnR^5$, —$B(R^4)_2$, —$B(OH)_2$, an amide, an imide, or an organometallic, it is also contemplated that $R^1$ is defined as an alkyl, an aryl, —$SiR^4$, —$SnR^5$, —$B(R^4)_2$, or —$B(OH)_2$.

The compounds of this invention are limited to those that are chemically feasible and stable. Therefore, a combination of substituents or variables in the compounds described above is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

A list following the word "comprising" is inclusive or open-ended, i.e., the list may or may not include additional unrecited elements. A list following the words "consisting of" is exclusive or closed ended, i.e., the list excludes any element not specified in the list.

The method of treating a condition, disorder or disease with a chemical compound or a chemical composition includes the use of the chemical compound or chemical composition in the manufacture of a medicament for the treatment of the condition, disorder or disease. A compound or a group of compounds said to be effective in treating a condition, disorder or disease includes the compound or group of compounds for use in treating the condition, disorder or disease.

Another embodiment of the invention relates to a method of treating cancer, comprising administering to a patient in need thereof an effective amount of a compound of Formula I or a compound below:

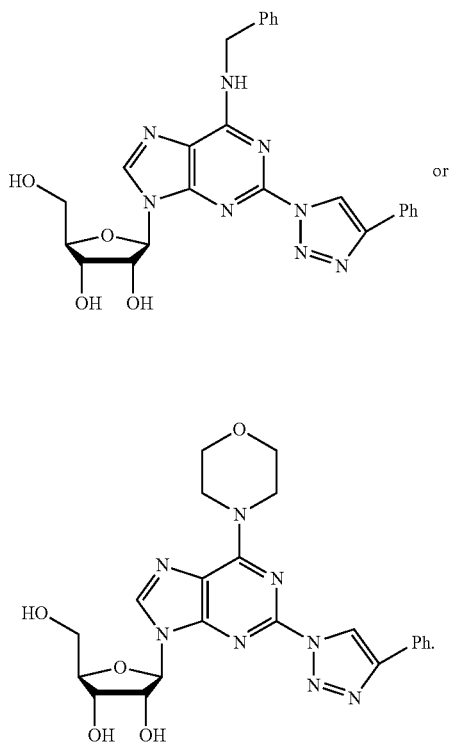

An effective amount of a compound of formula (I) or a pharmaceutically acceptable salt thereof as used herein is any amount effective to treat a patient infected by cancer. Modes of administration and doses can be determined by those having skill in the art. An effective amount of the compound will vary with the group of patients (age, sex, weight, etc.), the nature and severity of the condition to be treated, the particular compound administered, and its route of administration. Amounts suitable for administration to humans are routinely determined by physicians and clinicians during clinical trials.

The minimum dose of the compound is the lowest dose at which efficacy is observed. For example, the minimum dose of the compound may be about 0.1 mg/kg/day, about 1 mg/kg/day, or about 3 mg/kg/day.

The maximum dose of the compound is the highest dose at which efficacy is observed in a patient, and side effects are tolerable. For example, the maximum dose of the compound may be about 10 mg/kg/day, about 9 mg/kg/day, or about 8 mg/kg/day. In another embodiment, the maximum dose of the compound may be up to about 50 mg/kg/day.

A 1,2,3-triazolyl purine derivative useful in the methods of the present invention may be administered by any method known in the art. Some examples of suitable modes of administration include oral and systemic administration. Systemic administration can be enteral or parenteral. Liquid or solid (e.g., tablets, gelatin capsules) formulations can be employed.

Parenteral administration of the 1,2,3-triazolylpurine derivative include, for example intravenous, intramuscular, and subcutaneous injections. For instance, a chemical compound may be administered to a patient by sustained release, as is known in the art. Sustained release administration is a method of drug delivery to achieve a certain level of the drug over a particular period of time.

Other routes of administration include oral, topical, intrabronchial, or intranasal administration. For oral administration, liquid or solid formulations may be used. Some examples of formulations suitable for oral administration include tablets, gelatin capsules, pills, troches, elixirs, suspensions, syrups, and wafers. Intrabronchial administration can include an inhaler spray. For intranasal administration, administration of a chemical compound can be accomplished by a nebulizer or liquid mist.

The chemical compound can be formulated in a suitable pharmaceutical carrier. In this specification, a pharmaceutical carrier is considered to be synonymous with a vehicle or an excipient as is understood by practitioners in the art. Examples of carriers include starch, milk, sugar, certain types of clay, gelatin, stearic acid or salts thereof, magnesium or calcium stearate, talc, vegetable fats or oils, gums and glycols.

The chemical compound can be formulated into a composition containing one or more of the following: a stabilizer, a surfactant, preferably a nonionic surfactant, and optionally a salt and/or a buffering agent.

The stabilizer may, for example, be an amino acid, such as for instance, glycine; or an oligosaccharide, such as for example, sucrose, tetralose, lactose or a dextran. Alternatively, the stabilizer may be a sugar alcohol, such as for instance, mannitol; or a combination thereof. Preferably the stabilizer or combination of stabilizers constitutes from about 0.1% to about 10% weight for weight of the chemical compound.

The surfactant is preferably a nonionic surfactant, such as a polysorbate. Some examples of suitable surfactants include Tween 20, Tween 80; a polyethylene glycol or a polyoxyethylene polyoxypropylene glycol, such as Pluronic F-68 at from about 0.001% (w/v) to about 10% (w/v). Other preferred surfactants include Solutol H-15 and Cremophore EL.

The salt or buffering agent may be any salt or buffering agent, such as for example sodium chloride, or sodium/potassium phosphate, respectively. Preferably, the buffering agent maintains the pH of the chemical compound formulation in the range of about 5.5 to about 7.5. The salt and/or buffering agent is also useful to maintain the osmolality at a level suitable for administration to a patient. Preferably the salt or buffering agent is present at a roughly isotonic concentration of about 150 mM to about 300 mM.

The chemical compound can be formulated into a composition which may additionally contain one or more conventional additives. Some examples of such additives include a solubilizer such as, for example, glycerol; an antioxidant such as for example, benzalkonium chloride (a mixture of quaternary ammonium compounds, known as "quart"), benzyl alcohol, chloretone or chlorobutanol; anaesthetic agent such as, for example a morphine derivative; or an isotonic agent etc. As a further precaution against oxidation or other spoilage, the composition may be stored under nitrogen gas in vials sealed with impermeable stoppers.

Synthesis of C-2 Triazolylinosine and 2'-Deoxyinosine Derivatives

Scheme 1 shows the synthesis of protected $O^6$-allyl-2-azidoinosine and $O^6$-allyl-2-azido-2'-deoxyinosine. An azido group was installed at the C-2 position by diazotization of the amino group with t-BuONO in the presence of TMS—$N_3$.

Scheme 1. Synthesis of Protected O⁶-Allyl-2-azidoinosine and O⁶-Allyl-2-azido-2′-deoxyinosine

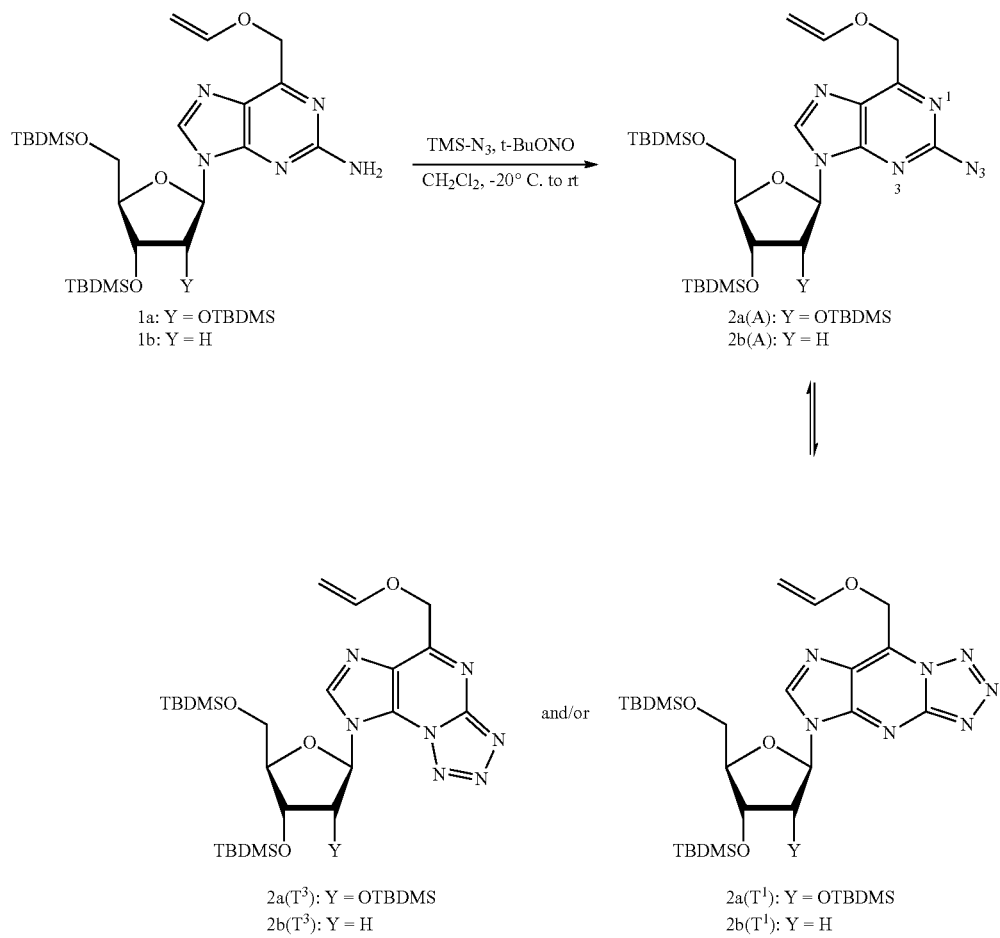

Silyl-protected O⁶-allyl-2-azidoinosine 2a(A) and the 2′-deoxyinosine analogue 2b(A) could be synthesized via this procedure in ca. 60% yield. C-2 azido derivatives of purines and purine nucleosides can exist in equilibrium with two possible tetrazolyl isomers. Similarly, 2a,b can exist as two tautomers termed 2a,b($T^1$) and 2a,b($T^3$), depending upon the nitrogen atom of the purine that is involved.

With the synthesis of the C-2 azido derivatives 2a,b completed, conditions for effectuating their ligation reactions with alkynes were evaluated (Table 1).

TABLE 1

Optimization of Azide-alkyne Ligation Conditions Using Trisilyl O⁶-Allyl-2-azidoinosine 2a and Phenylacetylene$^a$

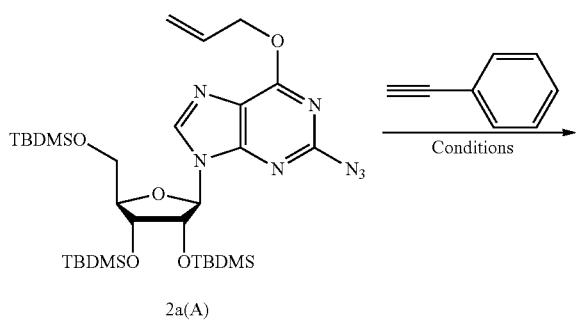

TABLE 1-continued

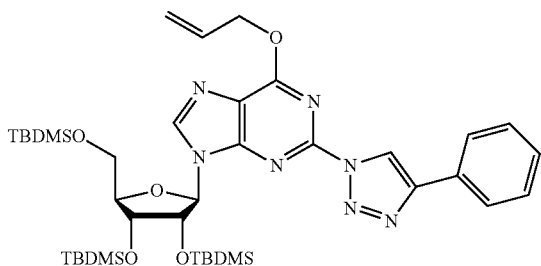

3

| entry | catalytic system | solvent (1:1) | time (h) | % yield of 3[b] |
|---|---|---|---|---|
| 1 | 20 mol % CuSO$_4$/40 mol % Na | CH$_2$Cl$_2$/H$_2$O | 24 | 30 (60% of 2a recovered) |
| 2 | 20 mol % CuSO4/40 mol % Na | t-BuOH/H2O | 36 | 54 |
| 3 | 20 mol % Cu(I) thiophene-2- | t-BuOH/H2O | 48 | 68 |
| 4 | 20 mol % CuCl | t-BuOH/H2O | 36 | 82 |

[a]Conditions: 0.1M 2a in the solvents indicated, room temperature (reactions were monitored for completion by TLC analysis).
[b]Yield of isolated and purified product.

Azidealkyne ligation chemistry was applied to the ribose derivative 2a as well as the 2′-deoxy analogue 2b. The results are summarized in Table 2.

TABLE 2

Azide-alkyne Ligation Reactions of Nucleosides 2a and 2b[a]

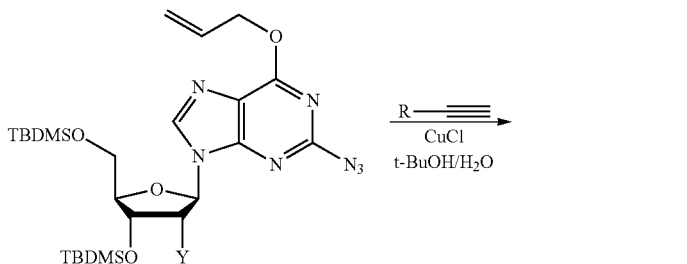

2a(A): Y = OTBDMS
2b(A): Y = H

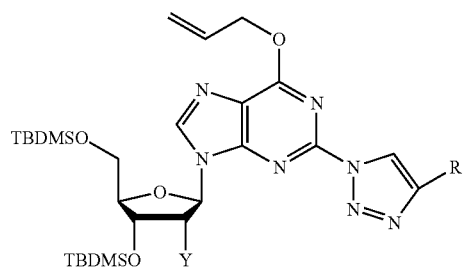

3-10: Y = OTBDMS
11-16: Y = H

| entry | substrate | alkyne | reaction time (h) | product: % yield[b] |
|---|---|---|---|---|
| 1 | 2a | 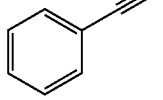 | 36 | 3: 82 |
| 2 | 2b | | 34 | 11: 74 |

TABLE 2-continued

Azide-alkyne Ligation Reactions of Nucleosides 2a and 2b[a]

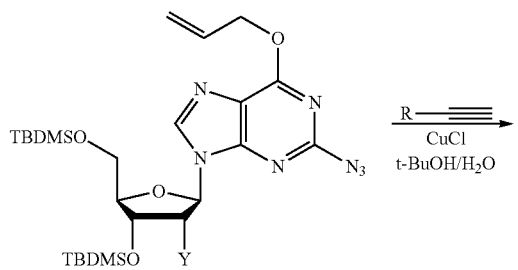

2a(A): Y = OTBDMS
2b(A): Y = H

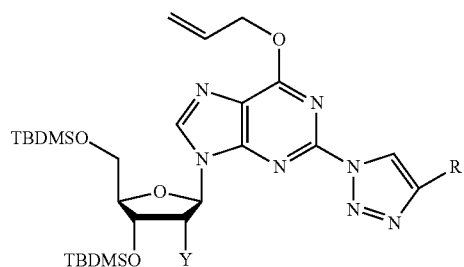

3-10: Y = OTBDMS
11-16: Y = H

| entry | substrate | alkyne | reaction time (h) | product: % yield[b] |
|---|---|---|---|---|
| 3 | 2a | 4-ethynyltoluene | 48 | 4: 79 |
| 4 | 2a | 4-ethynylanisole | 48 | 5: 78 |
| 5 | 2b | 4-ethynylanisole | 24 | 12: 78 |
| 6 | 2a | propargyl alcohol | 28 | 6: 79 |
| 7 | 2b | propargyl alcohol | 24 | 13: 70 |
| 8 | 2a | N-propargylphthalimide | 48 | 7: 82 |
| 9 | 2b | N-propargylphthalimide | 36 | 14: 73 |
| 10 | 2a | ethynylferrocene | 48 | 8: 78 |
| 11 | 2b | ethynylferrocene | 24 | 15: 72 |
| 12 | 2a | 1-hexyne | 44 | 9: 75 |
| 13 | 2b | 1-hexyne | 24 | 16: 71 |

TABLE 2-continued

Azide-alkyne Ligation Reactions of Nucleosides 2a and 2b[a]

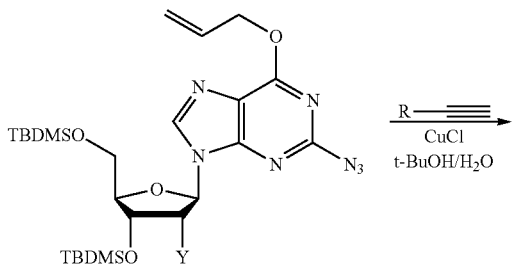

2a(A): Y = OTBDMS
2b(A): Y = H

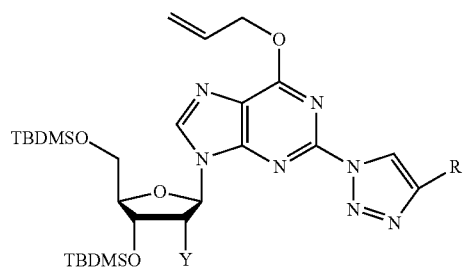

3-10: Y = OTBDMS
11-16: Y = H

| entry | substrate | alkyne | reaction time (h) | product: % yield[b] |
|---|---|---|---|---|
| 14 | 2a | (4-fluorophenyl acetylene) | 48 | 10: 71 |

[a]Conditions: 0.5M 2a or 2b in 1:1 t-BuOH/H2O, 20 mol % of CuCl, room temperature (reactions were monitored for completion by TLC analysis).
[b]Yields are of isolated and purified products.

The ensuing products were subjected to deprotection and Scheme 2 shows the protocol adopted for this purpose. First desilylation was conducted with fluoride ion and next deallylation was conducted with a palladium catalyst.

Scheme 2 shows the deprotection of the compounds.

Scheme 2. Deprotection of O$^6$-Allyl C-2 Triazolylinosine 2′-Deoxyinosine Analogues

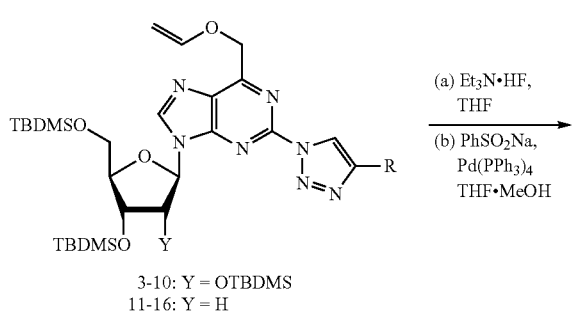

3-10: Y = OTBDMS
11-16: Y = H

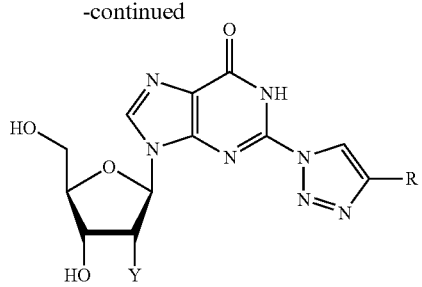

17-24: Y = OH
25-30: Y = H

Synthesis of C-2 Triazolyladenosine Derivatives

As shown in Scheme 3, deallylation of 3 followed by exposure of the resulting silyl-protected C-2 triazolylinosine derivative to 1H-benzotriazol-1-yloxytris(dimethylamino)-phosphonium hexafluorophosphate (BOP) and iPr$_2$NEt in THF at room temperature led to the formation of the corresponding O$^6$-(benzotriazolyl) derivative 31 in 55% yield. Reactions of 31 with morpholine and benzyl amine were conducted in 1,2-dimethoxyethane (DME) to yield the adenosine derivatives 32 and 33 in 77% and 90% yields, respectively. The products were then desilylated to yield the C2 triazolyl adenosine analogues 34 and 35.

Scheme 3. Synthesis of C-2 Triazolyladenosine Analogues via O⁶-Benzotriazolyl Derivatives

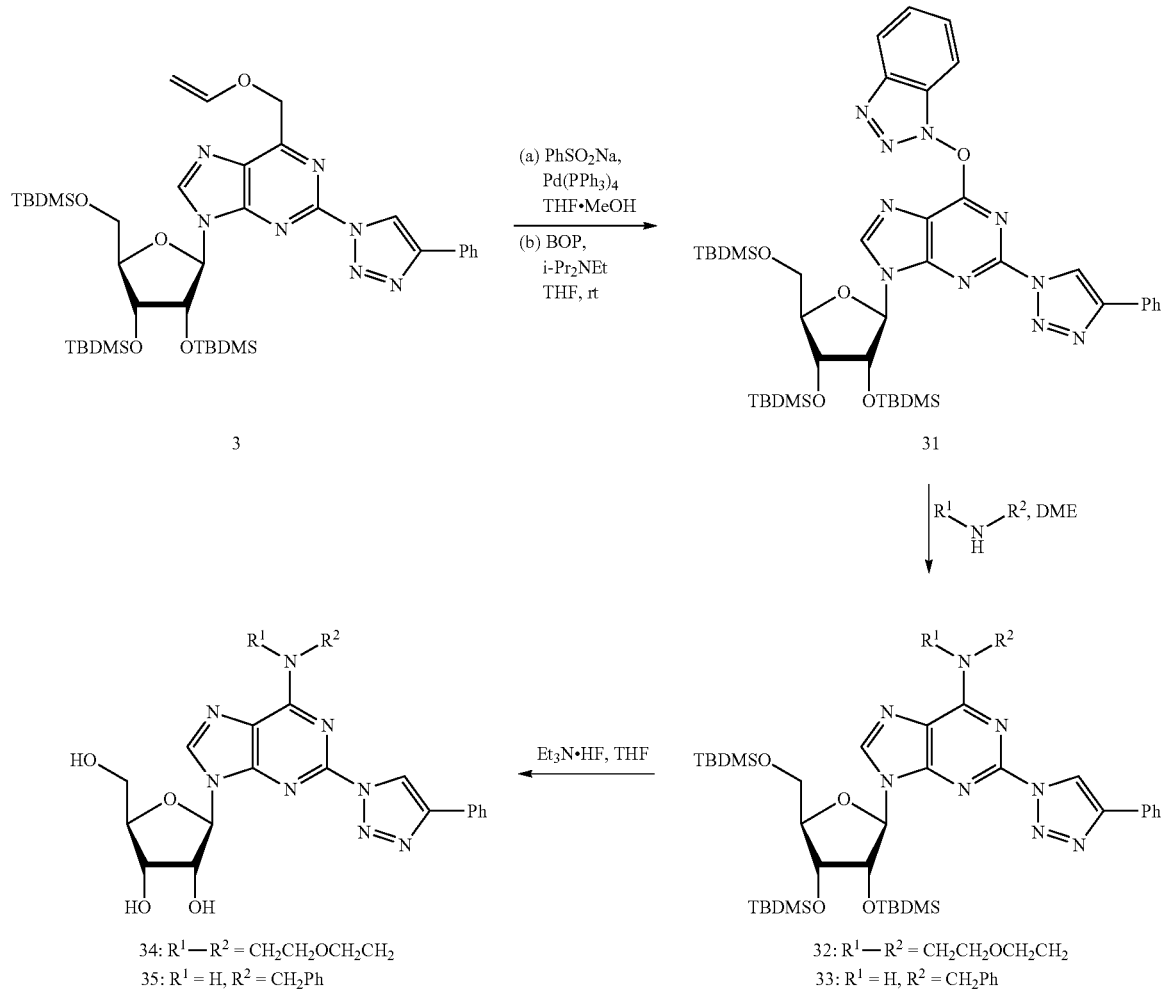

Synthesis of a Doubly Reactive Purine Nucleoside Derivative

A 2-azido-$O^6$-(benzotriazol-1H-yl)purine nucleoside derivative was synthesized. $O^6$-(benzotriazol-1H-yl)-2',3',5'-tri-O-(tert-butyldimethylsilyl)-guanosine (37) was diazotized with t-BuONO/TMS—$N_3$ (Scheme 4). The reaction gave a 49% unoptimized yield of 38 indicating the general stability of the $O^6$-(benzotriazol-1H-yl) group to the reaction conditions.

Scheme 4. Synthesis of Difunctionalizable Purine Nucleoside Derivative

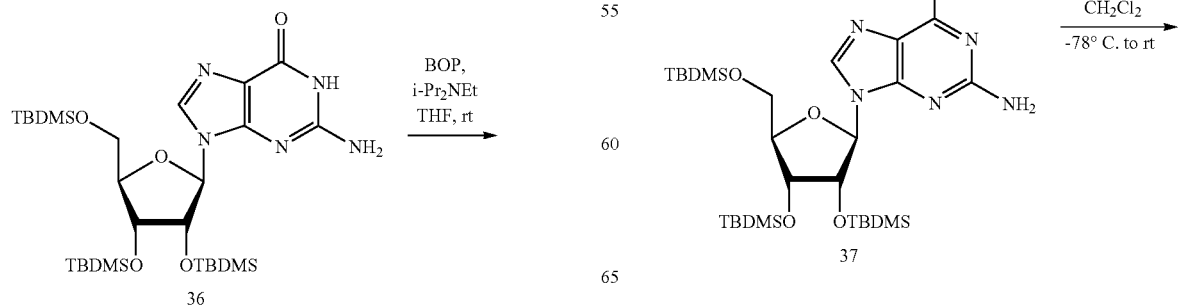

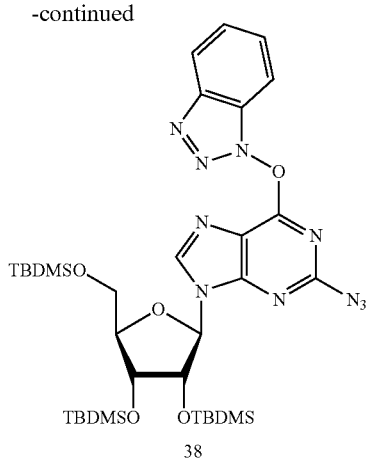

38

EXAMPLES

Examples have been set forth below for the purposes of illustration and to describe the best mode of the invention at the present time. The scope of the invention is not to be in any way limited by the examples set forth herein.

Example 1

Biological Activities of the Compounds

The compounds were evaluated for their antiviral activity against a broad variety of DNA and RNA viruses. Several compounds (I.e., 18, 22, and 25, see Table 3) showed marginal activity against cytomegalovirus (CMV), whereas the anti-CMV activity of 23 was somewhat more pronounced. The inosine derivative 23 showed activity against CMV in human embryonic lung (HEL) cells at an $EC_{50}$ of 39-73 µM. None of the compounds showed antiviral activity against other viruses at subtoxic concentrations except the inosine derivative 17 that was endowed with moderate antivesicular stomatitis virus (VSV) activity (27±2.4 µM) in human cervix carcinoma HeLa cell cultures. This activity could not be confirmed in human embryonic lung (HEL) fibroblast cell cultures against the same virus, making the moderate activity rather cell-type specific. Yet, in the HeLa and HEL cell cultures toxicity of 17 was observed at 100-240 µM. This may also mean that the anti-VSV activity noticed for 17 in the VSV/HeLa cell assay can be due to underlying toxicity to the host cells, rather than to a specific antiviral activity of the compound. From the antiviral assay systems performed, compound 34 had the highest impact on mammalian cell morphology, but this highly depended on the nature of the cell line used as the virus host [minimum detectable morphology-altering (cytotoxic) concentration (MCC): 8.3 µM against canine kidney MDCK, 42 µM against HeLa, 83 µM against feline kidney CRFK, 210 µM against green monkey kidney Vero, and ≥40 µM against HeLa cells].

The inosine derivatives 17-24 and 2'-deoxyinosine derivatives 25-30 were also evaluated for their cytostatic activity against murine leukemia L1210, human lymphocyte CEM, and HeLa cells. Modest cytostatic activity was noticed for several compounds. In particular, the HeLa cells were usually somewhat more sensitive to the inhibitory potential of these compounds than the other cell lines. Also, the ribose derivatives were consistently more cytostatic than their corresponding 2'-deoxyribose derivatives. Among all compounds tested, 17 proved most cytostatic, irrespective the nature of the tumor cell line ($IC_{50}$: 34-124 µM). Both adenosine derivatives 34 and 35 were poorly cytostatic ($IC_{50}$ for 34 98-185 µM, for 35 90-120 µM).

See Example 40 for the protocol of the biological assays.

TABLE 3

Anti-CMV activity of the test compounds in HEL cell cultures

| | anti-CMV activity $EC_{50}$ (µM)[a] | | HEL cell effects (µM) | |
|---|---|---|---|---|
| compound | AD-169 strain | Davis strain | cell morphology (MDC)[b] | cell growth ($IC_{50}$)[c] |
| 17 | >50 | >50 | 240 | nd[d] |
| 18 | 118 | 151 | >240 | 2240 |
| 19 | 2230 | 2230 | >230 | >230 |
| 20 | >270 | >270 | >270 | nd[d] |
| 21 | 2200 | >200 | >200 | >200 |
| 22 | 120 | 123 | 2190 | 123 |
| 23 | 73 | 39 | 2260 | >250 |
| 24 | >230 | >230 | >230 | nd[d] |
| 25 | 2250 | 158 | >250 | 188 |
| 26 | >240 | >240 | >240 | nd[d] |
| 27 | >290 | >290 | >290 | nd[d] |
| 28 | >210 | >210 | >210 | nd[d] |
| 29 | 2200 | 2200 | >200 | >200 |
| 30 | >270 | >270 | >270 | nd[d] |
| 34 | >40 | >40 | 240 | nd[d] |
| 35 | >40 | >40 | 200 | nd[d] |

[a]Effective concentration required to reduce virus plaque formation by 50%. Virus input was 100 plaque-forming units (PFU).
[b]Minimum cytotoxic concentration that caused a microscopically detectable alteration of cell morphology.
[c]Concentration required to reduce cell growth by 50%.
[d]Not determined.

TABLE 4

$GI_{50}$ (µM) of the test compounds against ovarian (1A9), two paclitaxel-resistant (PTX10 and PTX22) ovarian, colorectal (HCT116), and p53KO HCT116 cancer cell lines

| compound | 1A9 | PTX10 | PTX22 | HCT116 | p53KO |
|---|---|---|---|---|---|
| 17 | 22.8 | >50 | 4.76 | >50 | >50 |
| 18 | 38.0 | >50 | 13.4 | >50 | >50 |
| 19 | 29.5 | >50 | 8.56 | >50 | >50 |
| 20 | 20.4 | >50 | 3.53 | >50 | 42.6 |
| 21 | 6.32 | >50 | 14.1 | >50 | >50 |
| 22 | 29.7 | >50 | 12.9 | >50 | >50 |
| 23 | 37.0 | >50 | 28.1 | >50 | >50 |
| 24 | 34.0 | >50 | 31.0 | >50 | >50 |
| 25 | 31.0 | >50 | 14.8 | >50 | >50 |
| 26 | 37.2 | >50 | 15.7 | >50 | >50 |
| 27 | 49.4 | >50 | 32.9 | >50 | >50 |
| 28 | 49.6 | >50 | 32.2 | >50 | >50 |
| 29 | 41.6 | >50 | 18.0 | >50 | >50 |
| 30 | 46.1 | >50 | 26.9 | >50 | >50 |
| 34 | 0.18 | 11.73 | 0.95 | 3.7 | 10.4 |
| 35 | 5.0 | >50 | 24.5 | 43.61 | >50 |
| paclitaxel | 1.51 nM | 79 nM | 68 nM | 6.85 nM | 8.58 nM |

Example 2

$O^6$-Allyl-2',3',5'-tri-O-(tert-butyldimethylsilyl)guanosine (1a)

In a clean, dry 100 mL round-bottomed flask equipped with a stirring bar were placed $O^6$-(benzotriazol-1H-yl)-2',3',5'-tri-O-(tert-butyldimethylsilyl)guanosine (5.0 g, 6.7 mmol), allyl alcohol (50 mL) and $Cs_2CO_3$ (4.74 g, 14.1 mmol). The reaction mixture was flushed with nitrogen gas and stirred at room temperature for 2 h after which the mixture was evaporated to dryness. Chromatographic purification of the crude material on a silica gel column using 20% EtOAc in hexanes afforded 3.60 g (81% yield) of 1a as a white foam. $R_f$ (SiO$_2$/ 20% EtOAc in hexanes)=0.52. $^1$H NMR (CDCl$_3$): δ 7.96 (s, 1H, Ar—H), 6.16-6.08 (m, 1H, =CH), 5.92 (d, 1H, H-1', J=5.3 Hz), 5.41 (dd, 1H, =CH$_{trans}$, trans, J=1.4, 17.2 Hz), 5.25 (dd, 1H, =CH$_{cis}$, J=1.4, 10.2 Hz), 5.05 (s, 1H, NH$_2$), 4.98 (d, 2H, OCH$_2$, J=5.7 Hz), 4.48 (t, 1H, H-2', J=4.6 Hz), 4.27 (t, 1H, H-3', J=3.4 Hz), 4.09 (app q, 1H, H-4', J$_{app}$ ~3.2 Hz), 3.96 (dd, 1H, H-5', J=3.6, 11.4 Hz), 3.77 (dd, 1H, H-5', J=2.5, 11.4 Hz), 0.96, 0.95, and 0.82 (3s, 27H, t-Bu), 0.15, 0.14, 0.13, 0.12, 0.02, and 0.16 (6s, 18H, SiCH$_3$). $^{13}$C NMR (CDCl$_3$): δ 160.7, 159.1, 153.8, 137.7, 132.7, 118.0, 115.6, 87.5, 85.2, 76.2, 72.0, 67.2, 62.6, 26.0, 25.8, 25.6, 18.5, 18.0, 17.9, −4.3, −4.7, −5.0, −5.4. HRMS calculated for C$_{31}$H$_{60}$N$_5$O$_5$Si$_3$ [M+H]$^+$: 666.3897. found: 666.3909.

Example 3

O$^6$-Allyl-3',5'-di-O-(tert-butyldimethylsilyl)-2'-deoxyguanosine (1b)

As described for the synthesis of 1a, this compound was prepared by a reaction of O$^6$-(benzotriazol-1H-yl)-3',5'-di-O-(tert-butyldimethylsilyl)-2'-deoxyguanosine$^{25}$ (5.0 g, 8.16 mmol), allyl alcohol (50 mL) and Cs$_2$CO$_3$ (5.64 g, 17.1 mmol). Chromatographic purification of the crude material on a silica gel column using 30% EtOAc in hexanes) afforded 3.71 g (87% yield) of 1b as a white foam. $R_f$ (SiO$_2$/40% EtOAc in hexanes)=0.60. $^1$H NMR (CDCl$_3$): δ 7.93 (s, 1H, Ar—H), 6.34 (t, 1H, H-1', J=6.5 Hz), 6.17-6.09 (m, 1H, =CH), 5.43 (dd, 1H, =CH$_{trans}$, J=1.4, 17.2 Hz), 5.27 (dd, 1H, =CH$_{cis}$, J=1.4, 10.4 Hz), 5.01 (d, 2H, OCH$_2$, J=5.7 Hz), 4.94 (s, 1H, NH$_2$), 4.66-4.58 (m, 1H, H-3'), 3.99 (app q, 1H, H-4', J$_{app}$~3.5 Hz), 3.83 (dd, 1H, H-5', J=4.4, 11.2 Hz), 3.77 (dd, 1H, H-5', J=3.4, 11.2 Hz), 2.57 (app quint, 1H, H-2', J$_{app}$~6.5 Hz), 2.37 (ddd, 1H, H-2', J=4.0, 6.0, 13.0 Hz), 0.92 (s, 18H, t-Bu), 0.11 and 0.09 (2s, 12H, SiCH$_3$). $^{13}$C NMR (CDCl$_3$): δ 160.0, 159.2, 153.5, 137.8, 132.8, 118.4, 116.0, 87.8, 88.8, 72.1, 67.5, 63.0, 41.1, 26.1, 25.9, 18.6, 18.1, −4.4, −4.6, −5.2, −5.3. HRMS calculated for C$_{25}$H$_{46}$N$_5$O$_4$Si$_2$ [M+H]$^+$: 536.3083. found: 536.3093.

Example 4

O$^6$-Allyl-2-azido-2',3',5'-tri-O-(tert-butyldimethylsilyl)inosine (2a)

To a solution of 1a (3.0 g, 4.5 mmol) in dry CH$_2$Cl$_2$ (40 mL) at 20° C., TMS—N$_3$ (5.92 mL, 45.1 mmol) was added dropwise, followed by the addition of tet-BuONO (5.67 mL, 45.1 mmol). The reaction mixture was stirred at −20° C. for 1 h, then brought to room temperature, and allowed to stir for 24 h. The reaction mixture was diluted with MeOH:H$_2$O (1:1), allowed to stir for 1 h, and then extracted with CH$_2$Cl$_2$ (3×25 mL). The organic layer was washed with water and brine. Evaporation of the solvent followed by chromatographic purification on a silica gel column using 15% acetone in hexanes afforded 1.83 g (59% yield) of 2a as a thick, pale-yellow oil. $R_f$(SiO$_2$/20% EtOAc in hexanes)=0.60. IR (neat): 2958, 2927, 2857, 2929, 2856, 2126, 1597 cm$^{-1}$. $^1$H NMR (CDCl$_3$): δ 8.26 (s, 1H, Ar—H), 6.23-6.12 (m, 1H, =CH), 6.03 (d, 1H, H-1', J=4.8 Hz), 5.49 (dd, 1H, =CH$_{trans}$, J=1.2, 17.1 Hz), 5.34 (dd, 1H, =CH$_{cis}$, J=1.2, 10.3 Hz), 5.11 (d, 2H, OCH$_2$, J=5.9 Hz), 4.51 (t, 1H, H-2', J=4.4 Hz), 4.32 (t, 1H, H-3', J=4.4 Hz), 4.13 (app q, 1H, H-4', J$_{app}$~4.0 Hz), 4.03 (dd, 1H, H-5', J=3.9, 11.7 Hz), 3.77 (dd, 1H, H-5', J=2.5, 11.7 Hz), 0.95, 0.94, and 0.84 (3s, 27H, t-Bu), 0.17, 0.16, 0.12, 0.11, −0.02, and −0.14 (6s, 18H, SiCH$_3$). Resonances of the tetrazolyl form (<10%): δ 8.29 (s, 1H, Ar—H), 4.60 (t, 1H, H-2', J=4.4 Hz), 4.34 (t, 1H, H-3', J=4.4 Hz), 4.06 (d, 1H, H-5', J=4.2 Hz). $^{13}$C NMR (CDCl$_3$): δ 160.9, 155.8, 153.0, 140.8, 131.9, 119.1, 119.0, 88.3, 85.1, 76.0, 71.5, 68.1, 62.2, 26.1, 25.8, 25.6, 18.5, 18.0, 17.8, −4.4, −4.6, −4.8, −5.3. $^1$H NMR (DMSO-d$_6$): δ 8.53 (s, 1H, Ar—H), 6.17-6.09 (m, 1H, =CH), 5.92 (d, 1H, H-1', J=5.8 Hz), 5.46 (d, 1H, =CH$_{trans}$, J=17.2 Hz), 5.33 (d, 1H, =CH$_{cis}$, J=10.7 Hz), 5.06 (d, 2H, OCH$_2$, J=5.4 Hz), 4.82 (t, 1H, H-2', J=4.9 Hz), 4.32 (t, 1H, H-3', J=3.0 Hz), 4.00-3.98 (m, 1H, H-4'), 3.95 (dd, 1H, H-5', J=4.6, 11.2 Hz), 3.74 (dd, 1H, H-5', J=3.7, 11.2 Hz), 0.91, 0.90, and 0.74 (3s, 27H, t-Bu), 0.13, 0.11, 0.10, 0.08, −0.07, and −0.30 (6s, 18H, SiCH$_3$). Resonances of the tetrazolyl form (<10%): δ 8.63 (s, 1H, Ar—H), 4.89 (t, 1H, H-2' J=5.0 Hz), 4.38 (q, 1H, H-3' J=3.0 Hz). HRMS calculated for C$_{31}$H$_{58}$N$_7$O$_5$Si$_3$ [M+H]$^+$: 692.3802. found: 692.3808.

Example 5

O$^6$-Allyl-2-azido-3',5'-di-O-(tert-butyldimethylsilyl)-2'-deoxyinosine (2b)

As described for the synthesis of 2a, this compound was prepared by a reaction 1b (3.0 g, 5.6 mmol) with TMS—N$_3$ (10 molar equiv) and t-BuONO (10 molar equiv). Chromatographic purification of the crude material on a silica gel column using 20% EtOAc in hexanes afforded 1.98 g (63% yield) of 2b as a viscous, yellow oil. $R_f$(SiO$_2$/30% EtOAc in hexanes)=0.63. IR (neat): 2956, 2930, 2857, 2130, 1600 cm$^{-1}$. $^1$H NMR (CDCl$_3$): δ 8.18 (s, 1H, Ar—H), 6.42 (t, 1H, H-1', J=6.4 Hz), 6.18-6.11 (m, 1H, =CH), 5.49 (dd, 1H, =CH$_{trans}$, J=1.4, 17.2 Hz), 5.33 (dd, 1H, =CH$_{cis}$, J=1.4, 10.2 Hz), 5.11 (d, 2H, OCH$_2$, J=5.8 Hz), 4.61-4.59 (m, 1H, H-3'), 4.01 (app q, 1H, H-4', J$_{app}$~3.4 Hz), 3.88 (dd, 1H, H-5', J=4.0, 10.2 Hz), 3.79 (dd, 1H, H-5', J=3.0, 10.2 Hz), 2.56 (app quint, 1H, H-2', J$_{app}$~6.5 Hz), 2.43 (ddd, 1H, H-2', J=3.9, 5.9, 10.3 Hz), 0.93 and 0.92 (2s, 18H, t-Bu), 0.11 (s, 12H, SiCH$_3$). Resonances of the tetrazolyl form (<5%): δ 8.25 (s, 1H, Ar—H), 4.64-4.63 (m, 1H, H-3'), 2.64-2.62 (m, 1H, H-2'). $^{13}$C NMR (CDCl$_3$): δ 161.0, 155.8, 153.0, 140.6, 132.1, 119.3, 88.1, 84.5, 71.9, 68.6, 68.2, 62.9, 41.6, 26.1, 25.9, 18.5, 18.1, −4.4, −4.6, −5.3. $^1$H NMR (DMSO-d$_6$): δ 8.47 (s, 1H, Ar—H), 6.32 (t, 1H, H-1', J=6.4 Hz), 6.16-6.09 (m, 1H, =CH), 5.46 (d, 1H, =CH$_{trans}$, J=18.0 Hz), 5.33 (d, 1H, =CH$_{cis}$, J=10.7 Hz), 5.07 (d, 2H, OCH$_2$, J=5.4 Hz), 4.62 (m, 1H, H-3'), 3.58 (d, 1H, H-4', J=4.0 Hz), 3.78 (dd, 1H, H-5', J=5.9, 11.2 Hz), 3.67 (dd, 1H, H-5', J=4.4, 11.2 Hz), 2.90 (app quint, 1H, H-2', J$_{app}$~6.5 Hz), 2.34 (dd, 1H, H-2', J=5.2, 11.2 Hz), 0.93 and 0.83 (2s, 18H, t-Bu), 0.12, 0.01, and 0.0.1 (3s, 12H, SiCH$_3$). Resonances of the tetrazolyl form (<10%): δ 8.57 (s, 1H, Ar—H), 4.70 (m, 1H, H-3'), 0.81 (s, 18H, t-Bu), 0.13, 0.04, and −0.03 (3s, 12H, SiCH$_3$). HRMS calculated for C$_{25}$H$_{43}$N$_7$O$_4$Si$_2$Na [M+Na]$^+$: 584.2807 found: 584.2818.

Example 6

Typical Procedure for the Ligation Reactions of 2a

O$^6$-Allyl-2-(4-phenyl-1,2,3-triazol-1H-yl)-2',3',5'-tri-O-(tert-butyldimethylsilyl)inosine (3)

Azide 2a (492.0 mg, 0.711 mmol) and CuCl (14.0 mg. 0.2 mol %) were suspended in 8 mL of t-BuOH/H$_2$O (1:1), and reaction mixture was flushed with nitrogen gas. Phenyl acetylene (155 μL, 1.42 mmol) was added and the heterogeneous mixture was stirred at room temperature until TLC revealed no starting material (see Table 2 for reaction times). The reaction mixture was diluted with CH$_2$Cl$_2$ and washed with water followed by brine. The organic layer was dried over Na$_2$SO$_4$ and concentrated under reduced pressure. Chromatographic purification on a silica gel column using 20% EtOAc in hexanes afforded 461.0 mg (82% yield) of 3 as an off-white foam. R$_f$(SiO$_2$/20% EtOAc in hexanes)=0.57. $^1$H NMR (CDCl$_3$): δ 8.74 (s, 1H, Ar—H), 8.50 (s, 1H, Ar—H), 7.96 (d, 2H, Ar—H, J=7.8 Hz), 7.48 (t, 2H, Ar—H, J=7.3 Hz), 7.39 (t, 1H, Ar—H, J=7.3 Hz), 6.23-6.19 (m, 1H, =CH), 6.17 (d, 1H, H-1', J=4.4 Hz), 5.57 (dd, 1H, =CH$_{trans}$, J=1.0, 17.2 Hz), 5.37 (d, 1H, =CH$_{cis}$, J=10.3 Hz), 5.26 (d, 2H, OCH$_2$, J=6.3 Hz), 4.55 (t, 1H, H-2', J=4.4 Hz), 4.35 (t, 1H, H-3', J=4.2 Hz), 4.18 (br s, 1H, H-4'), 4.10 (dd, 1H, H-5', J=3.4, 11.7 Hz), 3.84 (dd, 1H, H-5', J=2.0, 11.7 Hz), 0.97, 0.94, and 0.83 (3s, 27H, t-Bu), 0.18, 0.16, 0.11, 0.10, −0.02, and −0.07 (6s, 18H, SiCH$_3$). $^{13}$C NMR (CDCl$_3$): δ 160.4, 151.8, 147.8, 147.0, 141.5, 131.1, 129.6, 128.2, 127.8, 125.3, 120.6, 119.6, 117.8, 88.1, 84.6, 75.8, 70.8, 68.2, 61.6, 25.5, 25.2, 25.0, 17.9, 17.5, 17.2, −4.9, −5.2, −5.3, −5.9. HRMS calculated for C$_{39}$H$_{64}$N$_7$O$_5$Si$_3$ [M+H]$^+$: 794.4271. found: 794.4281.

Example 7

O$^6$-Allyl-2-[4-(4-methylphenyl)-1,2,3-triazol-1H-yl]-2',3',5'-tri-O-(tert-butyldimethylsilyl)inosine (4)

Synthesized from 2a (413.0 mg, 0.597 mmol) and 4-ethynyltoluene (138 μL, 1.19 mmol). Chromatography of the crude reaction mixture on a silica gel column using 15% EtOAc in hexanes yielded 380.1 mg (79% yield) of 4 as a white, foamy solid. R$_f$(SiO$_2$/20% EtOAc in hexanes)=0.60. $^1$H NMR (CDCl$_3$): δ 8.70 (s, 1H, Ar—H), 8.50 (s, 1H, Ar—H), 7.85 (d, 2H, Ar—H, J=7.8 Hz), 7.30 (d, 2H, Ar—H, J=7.8 Hz), 6.25-6.17 (m, 1H, =CH), 6.16 (d, 1H, H-1', J=4.4 Hz), 5.56 (dd, 1H, =CH$_{trans}$, J=1.0, 17.1 Hz), 5.37 (dd, 1H, J=1.0, 10.1 Hz), 5.26 (d, 2H, OCH$_2$, J=6.3 Hz), 4.52 (t, 1H, H-2', J=4.4 Hz), 4.35 (t, 1H, H-3', J=4.2 Hz), 4.18 (q, 1H, H-4', J=3.0 Hz), 4.10 (dd, 1H, H-5', J=3.4, 11.2 Hz), 3.84 (dd, 1H, H-5', J=2.4, 11.2 Hz), 2.41 (s, 3H, CH$_3$), 0.97, 0.94, and 0.83, (3s, 27H, t-Bu), 0.18, 0.16, 0.11, 0.09, −0.02, and −0.06 (6s, 18H, SiCH$_3$). $^{13}$C NMR (CDCl$_3$): δ 161.0, 152.5, 148.6, 147.8, 142.2, 138.5, 131.9, 129.7, 129.1, 126.0, 121.2, 119.8, 118.2, 88.8, 85.3, 76.6, 71.5, 68.9, 62.3, 26.3, 26.0, 25.8, 21.4, 18.7, 18.2, 18.0, −4.1, −4.5, −4.6, −5.1. HRMS calculated for C$_{40}$H$_{66}$N$_7$O$_5$Si$_3$ [M+H]$^+$: 808.4428. found: 808.4435.

Example 8

O$^6$-Allyl-2-[4-(4-methoxyphenyl)-1,2,3-triazol-1H-yl]-2',3',5'-tri-O-(tert-butyldimethylsilyl)inosine (5)

Synthesized from 2a (403.0 mg, 0.582 mmol) and 4-ethynylanisole (154 μL, 1.16 mmol). Chromatography of the crude reaction mixture on a silica gel column using 20% EtOAc in hexanes yielded 373.3 mg (78% yield) of 5 as a white, foamy solid. R$_f$(SiO$_2$/20% EtOAc in hexanes)=0.46. $^1$H NMR (CDCl$_3$): δ 8.66 (s, 1H, Ar—H), 8.55 (s, 1H, Ar—H), 7.88 (d, 2H, Ar—H, J=8.3 Hz), 7.00 (d, 2H, Ar—H, J=8.3 Hz), 6.22 (m, 1H, =CH), 6.16 (d, 1H, H-1', J=3.9 Hz), 5.56 (d, 1H, =CH$_{trans}$, J=17.1 Hz), 5.36 (d, 1H, =CH$_{cis}$, J=10.3 Hz), 5.25 (d, 2H, OCH$_2$, J=5.7 Hz), 4.47 (br t, 1H, H-2', J=3.9 Hz), 4.33 (t, 1H, H-3', J=3.9 Hz), 4.18 (br s, 1H, H-4'), 4.10 (dd, 1H, H-5', J=2.9, 11.7 Hz), 3.86 (s, 3H, OCH$_3$), 3.83 (br d, 1H, H-5', J=11.7 Hz), 0.96, 0.91, and 0.82 (3s, 27H, t-Bu), 0.18, 0.15, 0.09, 0.079, −0.00, and −0.07 (6s, 18H, SiCH$_3$). $^{13}$C NMR (CDCl$_3$): δ 161.2, 160.0, 152.6, 148.6, 147.6, 142.2, 131.9, 127.4, 123.01, 121.3, 119.8, 117.7, 114.5, 88.7, 85.3, 76.6, 71.6, 68.9, 62.3, 55.5, 26.3, 26.0, 25.8, 18.7, 18.2, 18.0, −4.1, −4.9, −4.5, −4.6, −5.1, −5.2. HRMS calculated for C$_{40}$H$_{66}$N$_7$O$_6$Si$_3$ [M+H]$^+$: 824.4377. found: 824.4380.

Example 9

O$^6$-Allyl-2-[4-(hydroxymethyl-1,2,3-triazol-1H-yl]-2',3',5'-tri-O-(tert-butyldimethylsilyl)inosine (6)

Synthesized from 2a (368.0 mg, 0.532 mmol) and propargyl alcohol (61 μL, 1.06 mmol). Chromatography of the crude reaction mixture on a silica gel column using 40% EtOAc in hexanes yielded 311.3 mg (79% yield) of 6 as a white, foamy solid. R$_f$(SiO$_2$/40% EtOAc in hexanes)=0.48. $^1$H NMR (CDCl$_3$): δ 8.54 (s, 1H, Ar—H), 8.49 (s, 1H, Ar—H), 6.25-6.18 (m, 1H, =CH), 6.16 (d, 1H, H-1', J=4.3 Hz), 5.56 (dd, 1H, =CH$_{trans}$, J=1.5, 17.2 Hz), 5.38 (dd, 1H, =CH$_{cis}$, J=1.5, 10.3 Hz), 5.24 (d, 2H, OCH$_2$, J=5.6 Hz), 4.97 (s, 2H, CH$_2$), 4.58 (t, 1H, H-2', J=4.2 Hz), 4.35 (t, 1H, H-3', J=4.2 Hz), 4.19 (q, 1H, H-4', J=3.6 Hz), 4.09 (dd, 1H, H-5', J=3.6, 11.6 Hz), 3.85 (dd, 1H, H-5', J=2.0, 11.6 Hz), 0.99, 0.96, and 0.83 (3s, 27H, t-Bu), 0.20, 0.18, 0.13, 0.12, 0.02, and −0.11 (6s, 18H, SiCH$_3$). $^{13}$C NMR (CDCl$_3$): δ 161.1, 152.5, 148.5, 147.9, 142.4, 131.8, 121.9, 121.1, 119.7, 88.8, 85.5, 76.5, 71.7, 68.9, 62.4, 56.6, 26.2, 25.9, 25.7, 18.6, 18.2, 17.9, −4.1, −4.5, −4.6, −4.7, −5.2. HRMS calculated for C$_{34}$H$_{62}$N$_7$O$_6$Si$_3$ [M+H]$^+$: 748.4064. found: 748.4064.

Example 10

O$^6$-Allyl-2-[4-(N-phthalimidomethyl)-1,2,3-triazol-1H-yl]-2',3',5'-tri-O-(tert-butyldimethylsilyl)inosine (7)

Synthesized from 2a (418 mg, 0.604 mmol) and N-propargyl phthalimide (223.0 mg, 1.20 mmol). Chromatography of the crude reaction mixture on a silica gel column using 20% EtOAc in hexanes yielded 435.3 mg (82% yield) of 7 as an off-white, foamy solid. R$_f$(SiO$_2$/20% EtOAc in hexanes) =0.44. $^1$H NMR (CDCl$_3$): δ 8.53 (s, 1H, Ar—H), 8.49 (s, 1H, Ar-8), 7.89 (dd, 2H, Ar—H, J=3.2, 5.4 Hz), 7.74 (dd, 2H, Ar—H, J=3.2, 5.4 Hz), 6.22-6.14 (m, 1H, =CH), 6.10 (d, 1H, H-1', J=4.1 Hz), 5.56 (dd, 1H, =CH$_{trans}$, J=1.2, 17.2 Hz), 5.35 (br d, 1H, =CH$_{cis}$, J=10.4 Hz), 5.22 (d, 2H, OCH$_2$, J=5.9 Hz), 5.12 (s, 2H, NCH$_2$), 4.51 (t, 1H, H-2', J=4.0 Hz), 4.34 (t, 1H, H-3', J=4.0 Hz), 4.17 (app q, 1H, H-4', J$_{app}$~4.0 Hz), 4.10 (dd, 1H, H-5', J=3.5, 11.6 Hz), 3.82 (dd, 1H, H-5', J=2.6, 11.6 Hz), 0.96, 0.93, and 0.81 (3s, 27H, t-Bu), 0.17, 0.15, 0.11, 0.08, 0.00, and −0.10 (6s, 18H, SiCH$_3$). $^{13}$C NMR (CDCl$_3$): δ 167.6, 161.1, 152.4, 148.4, 143.0, 142.3, 142.3, 134.2, 132.2, 123.6, 122.1, 121.2, 119.8, 88.9, 85.2, 76.5, 71.4, 68.9, 62.2, 33.2, 26.2, 25.9, 25.7, 18.6, 18.2, 17.9, −4.1, −4.6, −5.1, −5.2. HRMS calculated for C$_{42}$H$_{65}$N$_8$O$_7$Si$_3$ [M+H]$^+$: 877.4279. found: 877.4293.

Example 11

O$^6$-Allyl-2-(4-ferrocenyl-1,2,3-triazol-1H-yl)-2',3',5'-tri-O-(tert-butyldimethylsilyl)inosine(8)

Synthesized from 2a (482.0 mg, 0.697 mmol) and ethynylferrocene (292.0 mg, 1.39 mmol). Chromatography of the crude reaction mixture on a silica gel column using 10% EtOAc in hexanes yielded 492.8 mg (78% yield) of 8 as a brown, foamy solid. $R_f$(SiO$_2$/20% EtOAc in hexanes)=0.62. $^1$H NMR (CDCl$_3$): δ 8.53 (s, 1H, Ar—H), 8.43 (s, 1H, Ar—H), 6.26-6.19 (m, 1H, =CH), 6.18 (d, 1H, H-1', J=3.9 Hz), 5.58 (br d, 1H, =CH$_{trans}$, J=17.1 Hz), 5.38 (br d, 1H, =CH$_{cis}$, J=10.4 Hz), 5.27 (d, 2H, OCH$_2$, J=5.8 Hz), 4.84 (app q, 1H, ferrocenyl-H, J$_{app}$~1.9 Hz), 4.82 (app q, 1H, ferrocenyl-H, J$_{app}$~1.9 Hz), 4.52 (t, 1H, H-2' J=4.3 Hz), 4.35 (d, 2H, ferrocenyl-H, J=1.9 Hz), 4.34 (t, 1H, H-3', J=3.9 Hz), 4.18 (br s, 1H, H-4'), 4.12 (s, 5H, ferrocenyl-H), 4.09 (dd, 1H, H-5', J=3.5, 11.5 Hz), 3.84 (dd, 1H, H-5', J=2.3, 11.5 Hz), 1.00, 0.96, and 0.87 (3s, 27H, t-Bu), 0.21, 0.19, 0.14, 0.12, 0.05, and −0.03 (6s, 18H, SiCH$_3$). $^{13}$C NMR (CDCl$_3$): δ 161.0, 152.4, 148.3, 146.9, 141.8, 131.8, 120.9, 119.7, 117.2, 88.5, 85.1, 76.6, 74.7, 71.3, 69.5, 68.8, 68.7, 66.8, 62.1, 26.1, 25.8, 25.6, 18.5, 18.0, 17.8, −4.3, −4.6, −4.7, −4.8, −5.3, −5.4 HRMS calculated for C$_{43}$H$_{68}$FeN$_7$O$_5$Si$_3$ [M+H]$^+$: 902.3934. found: 902.3936.

Example 12

O$^6$-Allyl-2-(4-n-butyl-1,2,3-triazol-1H-yl)-2',3',5'-tri-O-(tert-butyldimethylsilyl)inosine (9)

Synthesized from 2a (595.0 mg, 0.860 mmol) and propargyl alcohol (197 μL, 1.72 mmol). Chromatography of the crude reaction mixture on a silica gel column using 15% EtOAc in hexanes yielded 501.3 mg (75% yield) of 9 as a white, foamy solid. $R_f$(SiO$_2$/20% EtOAc in hexanes)=0.48. $^1$H NMR (CDCl$_3$): δ 8.48 (s, 1H, Ar—H), 8.26 (s, 1H, Ar—H), 6.25-6.17 (m, 1H, =CH), 6.16 (d, 1H, H-1', J=4.3 Hz), 5.56 (dd, 1H, =CH$_{trans}$, J=1.4, 17.2 Hz), 5.38 (dd, 1H, =CH$_{cis}$, J=1.4, 10.5 Hz), 5.25 (d, 2H, OCH$_2$, J=5.9 Hz), 4.54 (t, 1H, H-2', J=4.2 Hz), 4.35 (t, 1H, H-3', J=4.3 Hz), 4.18 (app q, 1H, H-4', J$_{app}$~3.5 Hz), 4.09 (dd, 1H, H-5', J=3.5, 11.5 Hz), 3.84 (dd, 1H, H-5', J=2.2, 11.5 Hz), 2.84 (t, 2H, butyl-CH$_2$, J=7.6 Hz), 1.75 (quint, 2H, butyl-CH$_2$, J=7.6 Hz), 1.46 (sextet, 2H, butyl-CH$_2$, J=7.5 Hz), 0.99 (t, 3H, butyl-CH$_3$, J=7.5 Hz), 0.98, 0.95, and 0.83 (3s, 27H, t-Bu), 0.19, 0.17, 0.12, 0.11, −0.02, and −0.09 (6s, 18H, SiCH$_3$). $^{13}$C NMR (CDCl$_3$): δ 161.3, 152.6, 148.8, 148.6, 142.2, 132.0, 121.2, 120.1, 119.8, 88.9, 85.4, 76.7, 71.7, 69.0, 62.5, 31.6, 26.4, 26.1, 25.9, 25.5, 22.5, 18.8, 18.3, 18.1, 14.0, −4.1, −4.4, −4.5, −4.6, −5.1. HRMS calculated for C$_{37}$H$_{68}$N$_7$O$_5$Si$_3$ [M+H]$^+$: 774.4584. found: 774.4582.

Example 13

O$^6$-Allyl-2-[4-(4-fluorophenyl)-1,2,3-triazol-1H-yl]-2',3',5'-tri-O-(tert-butyldimethylsilyl)inosine (10)

Synthesized from 2a (600.0 mg, 0.867 mmol) and 4-ethynylfluorobenzene (200 μL, 1.73 mmol). Chromatography of the crude reaction mixture on a silica gel column using 15% EtOAc in hexanes yielded 500.1 mg (71% yield) of 10 as an off-white, foamy solid. $R_f$(SiO$_2$/20% EtOAc in hexanes)=0.61. $^1$H NMR (CDCl$_3$): δ 8.70 (s, 1H, Ar—H), 8.52 (s, 1H, Ar—H), 7.95 (dd, 2H, Ar—H, J=5.3, 8.6 Hz), 7.19 (t, 2H, Ar—H, J=8.6 Hz), 6.27-6.19 (m, 1H, =CH), 6.08 (d, 1H, H-1', J=4.3 Hz), 5.57 (dd, 1H, =CH$_{trans}$, J=1.0, 17.2 Hz), 5.39 (dd, 1H, =CH$_{cis}$, J=1.0, 10.4 Hz), 5.29 (d, 2H, OCH$_2$, J=5.9 Hz), 4.57 (t, 1H, H-2', J=4.2 Hz), 4.37 (t, 1H, H-3', J=4.2 Hz), 4.20 (br s, 1H, H-4'), 4.11 (dd, 1H, H-5', J=3.6, 11.6 Hz), 3.82 (dd, 1H, H-5', J=2.1, 11.6 Hz), 0.99, 0.96, and 0.85 (3s, 27H, t-Bu), 0.20, 0.18, 0.13, 0.12, 0.04, and −0.06 (6s, 18H, SiCH$_3$). $^{13}$C NMR (CDCl$_3$): δ 164.1 and 162.1 (d, $^1$J=246.8 Hz), 161.2, 152.6, 148.5, 146.9, 142.4, 131.9, 128.0 and 127.9 (d, $^3$J=8.2 Hz), 126.6, 121.4, 119.8, 118.2, 116.2 and 116.0 (d, $^2$J=21.8 Hz), 88.8, 85.5, 76.7, 71.6, 69.0, 62.4, 26.3, 26.0, 25.8, 18.7, 18.3, 18.0, −4.1, −4.4, −4.5, −4.6, −5.1. HRMS calculated for C$_{39}$H$_{62}$FN$_7$O$_5$Si$_3$Na [M+Na]$^+$: 834.3996. found: 834.3993.

Example 14

O$^6$-Allyl-2-(4-phenyl-1,2,3-triazol-1H-yl)-3',5'-di-O-(tert-butyldimethylsilyl)-2'-deoxyinosine (11)

Synthesized from 2b (320.0 mg, 0.569 mmol) and phenyl acetylene (125 μL, 1.13 mmol). Chromatography of the crude reaction mixture on a silica gel column using 30% EtOAc in hexanes yielded 281.2 mg (74% yield) of 11 as an off-white, foamy solid. $R_f$(SiO$_2$/20% EtOAc in hexanes)=0.50. $^1$H NMR (CDCl$_3$): δ 8.76 (s, 1H, Ar—H), 8.41 (s, 1H, Ar—H), 7.99 (d, 2H, Ar—H, J=8.0 Hz), 7.49 (t, 2H, Ar—H, J=7.5 Hz), 7.40 (t, 1H, Ar—H, J=7.5 Hz), 6.64 (t, 1H, H-1', J=6.2 Hz), 6.26-6.19 (m, 1H, =CH), 5.58 (d, 1H, =CH$_{trans}$, J=17.2 Hz), 5.39 (d, 1H, =CH$_{cis}$, J=10.4 Hz), 5.27 (d, 2H, OCH$_2$, J=5.3 Hz), 4.68 (br s, 1H, H-3'), 4.07 (m, 1H, H-4'), 3.95 (br d, 1H, H-5', J=11.3 Hz), 3.79 (br d, 1H, H-5', J=11.3 Hz), 2.62 (app quint, 1H, H-2', J$_{app}$~6.5 Hz), 2.58-2.54 (m, 1H, H-2'), 0.95 (s, 18H, t-Bu), 0.14 (s, 12H, SiCH$_3$). $^{13}$C NMR (CDCl$_3$): δ 161.1, 152.5, 148.5, 147.9, 142.0, 131.9, 130.3, 129.0, 128.7, 126.2, 121.1, 119.8, 118.8, 88.3, 84.7, 71.9, 69.0, 62.9, 42.2, 26.2, 25.9, 18.6, 18.2, −4.3, −4.5, −5.1, −5.2. HRMS calculated for C$_{33}$H$_{49}$N$_7$O$_4$Si$_2$Na [M+Na]$^+$: 686.3277. found: 686.3285.

Example 15

O$^6$-Allyl-2-[4-(4-methoxyphenyl)-1,2,3-triazol-1H-yl]-3',5'-di-O-(tert-butyldimethylsilyl)-2'-deoxyinosine (12)

Synthesized from 2b (352.0 mg, 0.626 mmol) and 4-ethynylanisole (165 μL, 1.25 mmol). Chromatography of the crude reaction mixture on a silica gel column using 40% EtOAc in hexanes yielded 302.3 mg (78% yield) of 12 as an off-white, foamy solid. $R_f$(SiO$_2$/30% EtOAc in hexanes)=0.54. $^1$H NMR (CDCl$_3$): δ 8.67 (s, 1H, Ar—H), 8.42 (s, 1H, Ar—H), 7.91 (d, 2H, Ar—H, J=8.0 Hz), 7.02 (d, 2H, Ar—H, J=8.0 Hz), 6.64 (br s, 1H, H-1'), 6.17 (br m, 1H, =CH), 5.58 (d, 1H, =CH$_{trans}$, J=17.0 Hz), 5.38 (d, 1H, =CH$_{cis}$, J=10.3 Hz), 5.26 (br d, 2H, $_{OCH2}$, J=4.6 Hz), 4.68 (br s, 1H, H-3'), 4.06 (br s, 1H, H-4'), 3.94 (br d, 1H, H-5', J=11.2 Hz), 3.88 (s, 3H, OCH$_3$), 3.83 (br d, 1H, H-5', J=11.2 Hz), 2.64-2.54 (br m, 2H, H-2'), 0.94 (s, 18H, t-Bu), 0.14 (s, 12H, SiCH$_3$). $^{13}$C NMR (CDCl$_3$): 161.1, 160.0, 152.5, 148.6, 147.7, 142.1, 132.0, 127.5, 123.0, 121.2, 119.7, 117.9, 114.5, 88.3, 84.7, 71.9, 68.9, 62.9, 55.5, 42.1, 26.1, 25.9, 18.6, 18.2, −4.3, −4.5, −4.9, −5.3. HRMS calculated for C$_{34}$H$_{51}$N$_7$O$_5$Si$_2$Na [M+Na]$^+$: 716.3382. found: 716.3395.

Example 16

O$^6$-Allyl-2-[4-(hydroxymethyl)-1,2,3-triazol-1H-yl]-3',5'-di-O-(tert-butyldimethylsilyl)-2'-deoxyinosine (13)

Synthesized from 2b (350.0 mg, 0.622 mmol) and propargyl alcohol (272 μL, 1.24 mmol). Chromatography of the crude reaction mixture on a silica gel column using 50% EtOAc in hexanes yielded 272.1 mg (70% yield) of 13 as a white, foamy solid. $R_f$(SiO$_2$/40% EtOAc in hexanes)=0.21. $^1$H NMR (CDCl$_3$): δ 8.55 (s, 1H, Ar—H), 8.40 (s, 1H, Ar—H), 6.59 (t, 1H, H-1', J=6.3 Hz), 6.20-6.15 (m, 1H, =CH), 5.52 (d, 1H, =CH$_{trans}$, J=17.2 Hz), 5.34 (d, 1H, =CH$_{cis}$, J=10.4 Hz), 5.20 (d, 2H, OCH$_2$, J=5.9 Hz), 4.93 (d, 2H, CH$_2$, J=5.9 Hz), 4.65 (app q, 1H, H-3', J$_{app}$~4.5 Hz), 4.02 (br d, 1H, H-4' J=3.2 Hz), 3.91 (dd, 1H, H-5', J=3.5, 11.5 Hz), 3.80 (dd, 1H, H-5', J=2.7, 11.3 Hz), 3.01 (t, 1H, OH, J=5.9 Hz), 2.60 (app quint, 1H, H-2', J$_{app}$~6.5 Hz), 2.56-2.52 (ddd, 1H, H-2' J=4.5, 6.0, 10.6 Hz), 0.92 (s, 18H, t-Bu), 0.11 (s, 12H, SiCH$_3$). $^{13}$C NMR (CDCl$_3$): δ 161.1, 152.4, 148.4, 148.0, 142.2, 131.9, 121.4, 121.2, 119.7, 88.3, 84.7, 71.8, 68.9, 62.9, 56.8, 42.1, 26.1, 25.9, 18.6, 18.2, −4.4, −4.5, −5.1, −5.2. HRMS calculated for C$_{28}$H$_{47}$N$_7$O$_5$Si$_2$Na [M+Na]$^+$: 640.3069. found: 640.3077.

Example 17

O$^6$-Allyl-2-[4-(N-phthalimidomethyl)-1,2,3-triazol-1H-yl]-3',5'-di-O-(tert-butyldimethylsilyl)-2'-deoxyinosine (14)

Synthesized from 2b (365.0 mg, 0.649 mmol) and N-propargyl phthalimide (240 μL, 1.29 mmol). Chromatography of the crude reaction mixture on a silica gel column using 35% EtOAc in hexanes yielded 351.8 mg (73% yield) of 14 as a white, foamy solid. R$_f$(SiO$_2$/20% EtOAc in hexanes)=0.28. $^1$H NMR (CDCl$_3$): δ 8.56 (s, 1H, Ar—H), 8.39 (s, 1H, Ar—H), 7.88 (dd, 2H, Ar—H, J=3.0, 5.5 Hz), 7.74 (dd, 2H, Ar—H, J=3.0, 5.5 Hz), 6.57 (t, 1H, H-1', J=6.3 Hz), 6.21-6.13 (m, 1H, =CH), 5.53 (dd, 1H, =CH, J=1.4, 17.2 Hz), 5.34 (dd, 1H, =CH$_{cis}$, J=1.4, 10.4 Hz), 5.20 (d, 2H, OCH$_2$, J=5.9 Hz), 5.12 (s, 2H, NCH$_2$), 4.64 (app q, 1H, H-3', J$_{app}$~4.0), 4.02 (app q, 1H, H-4', J$_{app}$~3.3 Hz), 3.92 (dd, 1H, H-5', J=3.5, 11.3 Hz), 3.80 (dd, 1H, H-5', J=2.9, 11.3 Hz), 2.57 (app quint, 1H, H-2', J$_{app}$~6.5 Hz), 2.50 (ddd, 1H, H-2', J=4.5, 6.3, 10.6 Hz), 0.92 and 0.90 (2s, 18H, t-Bu), 0.12 and 0.10 (2s, 12H, SiCH$_3$). $^{13}$C NMR (CDCl$_3$): δ 167.5, 160.9, 152.1, 148.1, 142.8, 141.8, 134.1, 132.0, 131.7, 123.4, 122.2, 119.5, 88.1, 84.5, 71.6, 68.7, 62.6, 58.1, 41.9, 33.0, 25.9, 25.7, 18.4, 18.0, −4.6, −4.8, −5.3, −5.5. HRMS calculated for C$_{36}$H$_{50}$N$_8$O$_6$Si$_2$Na [M+Na]$^+$: 769.3284. found: 769.3290.

Example 18

O$^6$-Allyl-2-(4-ferrocenyl-1,2,3-triazol-1H-yl)-3',5'-di-O-(tert-butyldimethylsilyl)-2'-deoxyinosine (15)

Synthesized from 2b (595.0 mg, 1.05 mmol) and ethynylferrocene (444 μL, 2.11 mmol). Chromatography of the crude reaction mixture on a silica gel column using 20% EtOAc in hexanes yielded 620.2 mg (72% yield) of 15 as a reddish-brown, foamy solid. R$_f$(SiO$_2$/30% EtOAc in hexanes)=0.30. $^1$H NMR (CDCl$_3$): δ 8.40 (s, 1H, Ar—H), 8.35 (s, 1H, Ar—H), 6.64 (br s, 1H, H-1'), 6.23 (br m, 1H, =CH), 5.57 (d, 1H, =CH$_t$, J=17.0 Hz), 5.40 (d, 1H, =CH$_{cis}$, J=10.0 Hz), 5.26 (br s, 2H, OCH$_2$), 5.04 (br s, 2H, ferrocenyl-H), 4.66 (br s, 1H, H-3'), 4.54 (br s, 2H, ferrocenyl-H), 4.28 (br s, 5H, ferrocenyl-H), 4.06 (br s, 1H, H-4'), 3.93 (dd, 1H, H5', J=3.0, 11.2 Hz), 3.82 (dd, 1H, H-5', J=2.0, 11.2 Hz), 2.59-2.57 (br m, 2H, H-2'), 0.95 and 0.94 (2s, 18H, t-Bu), 0.14 and 0.13 (2s, 12H, SiCH$_3$). $^{13}$C NMR (CDCl$_3$) δ 161.2, 152.6, 148.7, 147.3, 142.0, 132.1, 121.1, 119.8, 117.7, 88.4, 84.6, 72.0, 69.8, 69.1, 69.0, 67.2, 67.1, 63.0, 42.3, 26.2, 26.0, 18.7, 18.3, −4.4, −4.6, −5.1, −5.3. HRMS calculated for C$_{37}$H$_{54}$FeN$_7$O$_4$Si$_2$ [M+H]$^+$: 772.3120. found: 772.3126.

Example 19

O$^6$-Allyl-2-(4-n-butyl-1,2,3-triazol-1H-yl)-3',5'-di-O-(tert-butyldimethylsilyl)-2'-deoxyinosine (16)

Synthesized from 2b (393.0 mg, 0.699 mmol) and 1-hexyne (160 μL, 1.39 mmol). Chromatography of the crude reaction mixture on a silica gel column using 20% EtOAc in hexanes yielded 320.1 mg (71% yield) of 16 as a white, foamy solid. R$_f$(SiO$_2$/20% EtOAc in hexanes)=0.40. $^1$H NMR (CDCl$_3$): δ 8.41 (s, 1H, Ar—H), 8.28 (s, 1H, Ar—H), 6.62 (t, 1H, H-1', J=6.3 Hz), 6.23-6.15 (m, 1H, =CH), 5.53 (dd, 1H, =CH$_{trans}$, J=1.4, 17.2 Hz), 5.36 (dd, 1H, =CH$_{cis}$, J=1.4, 10.4 Hz), 5.22 (d, 2H, OCH$_2$, J=5.9 Hz), 4.64 (m, 1H, H-3'), 4.02 (app q, 1H, H-4', J$_{app}$~3.5 Hz), 3.92 (dd, 1H, H-5', J=3.4, 11.3 Hz), 3.81 (dd, 1H, H-5', J=2.7, 11.3 Hz), 2.83 (t, 2H, butyl-CH$_2$, J=7.7 Hz), 2.57 (app quint, 1H, H-2', J$_{app}$~6.5 Hz), 2.52 (ddd, 1H, H-2', J=4.3, 6.3, 11.0 Hz), 1.74 (quint, 2H, butyl-CH$_2$, J=7.5 Hz), 1.44 (sextet, 2H, butyl-CH$_2$, J=7.5 Hz), 0.96 (t, 3H, butyl-CH$_3$, J=7.5 Hz), 0.93 and 0.92 (2s, 18H, t-Bu), 0.12 and 0.11 (2s, 12H, SiCH$_3$). $^{13}$C NMR (CDCl$_3$): δ 160.9, 152.3, 148.6, 1485, 141.9, 131.8, 120.9, 120.0, 119.5, 88.1, 84.5, 71.7, 68.7, 62.8, 41.9, 31.5, 26.0, 25.8, 25.3, 22.3, 18.5, 18.0, 13.8, −4.5, −4.7, −5.3, −5.4. HRMS calculated for C$_{31}$H$_{54}$N$_7$O$_4$Si$_2$ [M+H]$^+$: 644.3770. found: 644.3777.

Example 20

Typical Procedure for Disilylation and Deallylation Reactions of the Triazolyl Nucleosides 2-[4-(Phenyl)-1,2,3-triazol-1H-yl]inosine (17)

Step 1: Disilylation.

Et$_3$N.3HF (389 μL, 2.39 mmol) was added to a solution of 3 (380.0 mg, 0.47 mmol) in dry THF (5.0 mL), and the reaction mixture was stirred at room temperature for 24 h. The mixture was evaporated under a stream of nitrogen gas using a polypropylene pipet. The crude product was purified by chromatography on silica gel column using 10% MeOH in EtOAc to give 171.2 mg (80% yield) of the O$^6$-allyl-protected nucleoside as colorless, amorphous solid. R$_f$(SiO$_2$/10% MeOH in EtOAc)=0.31. $^1$H NMR (DMSO-d$_6$): δ 9.42 (s, 1H, Ar—H), 8.74 (s, 1H, Ar—H), 8.00 (d, 2H, Ar—H, J=8.3 Hz), 7.52 (t, 2H, Ar—H, J=7.5 Hz), 7.43 (t, 1H, Ar—H, J=7.5 Hz), 6.26-6.15 (m, 1H, =CH), 6.08 (d, 1H, H-1', J=5.8 Hz), 5.64 (br s, 1H, OH), 5.56 (dd, 1H, =CH$_{trans}$, J=1.6, 17.2 Hz), 5.39 (br d, 1H, =CH$_{cis}$, J=17.2 Hz), 5.37 (br s, 1H, OH), 5.28 (d, 2H, OCH$_2$, J=5.8 Hz), 5.11 (t, 1H, OH, J=5.3 Hz), 4.66 (br s, 1H, H-2'), 4.23 (br s, 1H, H-3'), 4.01 (app q, 1H, H-4', J$_{app}$~3.6 Hz), 3.71 (ddd, 1H, H-5', J=2.8, 7.2, 11.2 Hz), 3.63 (ddd, 1H, H-5', J=5.0, 7.2, 11.2 Hz).

Step 2: Deallylation.

A solution of PhSO$_2$Na (14.5 mg, 0.088 mmol) in MeOH (1.0 mL) was added to a suspension of the desilylated product obtained in step 1 (40.0 mg, 0.088 mmol) and Pd(PPh$_3$)$_4$ (5.1 mg, 5 mol %) in dry THF (2.0 mL), at room temperature. The reaction mixture was stirred at room temperature for 2 h at which time TLC revealed no starting material. The reaction mixture was concentrated under reduced pressure and triturated with EtOAc to give 26.4 mg (72% yield) of 17 as a white solid. R$_f$(SiO$_2$/MeOH)=0.54. $^1$H NMR (DMSO-d$_6$): δ 9.07 (s, 1H, Ar—H), 8.01 (s, 1H, Ar—H), 7.98 (d, 2H, Ar—H, J=7.8 Hz), 7.48 (t, 2H, Ar—H, J=7.3 Hz), 7.36 (t, 1H, Ar—H, J=7.3 Hz), 5.86 (d, 1H, H-1', J=6.3 Hz), 5.46 (d, 1H, OH, J=6.3 Hz), 5.20 (d, 1H, OH, J=4.6 Hz), 5.08 (t, 1H, OH, J=6.0 Hz), 4.66 (app q, 1H, H-2', $J_{app}$~5.9 Hz), 4.19 (app q, 1H, H-3', $J_{app}$~4.0 Hz), 3.95 (q, 1H, H-4', J=3.4 Hz), 3.71-3.66 (m, 1H, H-5'), 3.59-3.54 (m, 1H, H-5'). $^{13}$C NMR (DMSO-d$_6$): δ 167.8, 151.5, 150.6, 147.4, 137.8, 131.9, 129.6, 128.8, 126.0, 125.5, 120.6, 87.9, 86.2, 73.9, 71.4, 62.5. HRMS calculated for $C_{18}H_{17}N_7O_5Na$ [M+Na]$^+$: 434.1183. found: 434.1200.

Example 21

2-[4-(4-Methylphenyl)-1,2,3-triazol-1H-yl]inosine (18)

Step 1: Desilylation.

Using the procedure described for the desilylation of 17, this compound was synthesized from 4 (300.0 mg, 0.371 mmol) and Et$_3$N.3HF (300 μL, 1.85 mmol). Chromatography of the crude reaction mixture on a silica gel column using 10% MeOH in EtOAc yielded 130.8 mg (76% yield) of the O$^6$-allyl-protected nucleoside as a white, foamy solid. R$_f$(SiO$_2$/10% MeOH in EtOAc)=0.27. $^1$H NMR (DMSO-d6): δ 9.37 (s, 1H, Ar—H), 8.74 (s, 1H, Ar—H), 7.95 (d, 2H, Ar—H, J=7.9 Hz), 7.32 (d, 2H, Ar—H, J=7.9 Hz), 6.26-6.18 (m, 1H, =CH), 6.08 (d, 1H, H-1', J=5.8 Hz), 5.57 (d, 1H, OH, J=5.4 Hz), 5.56 (br s, 1H, =CH$_{trans}$), 5.38 (d, 1H, =CH$_{cis}$, J=10.5 Hz), 5.31 (d, 1H, OH, J=5.6 Hz), 5.28 (d, 2H, OCH$_2$, J=5.7 Hz), 5.04 (t, 1H, OH, J=5.5 Hz), 4.66 (app q, 1H, H-2', $J_{app}$~5.5 Hz), 4.22 (app q, 1H, H-3', $J_{app}$~4.0 Hz), 4.00 (br d, 1H, H-4', J=3.5 Hz), 3.74-3.69 (m, 1H, H-5'), 3.63-3.59 (m, 1H, H-5'), 2.36 (s, 3H, CH$_3$).

Step 2: Deallylation.

The desilylated product (80.0 mg, 0.172 mmol) obtained in step 1 was deallylated as described for 17 using Pd(PPh$_3$)$_4$ (5.1 mg, 5 mol %) and PhSO$_2$Na (26.9 mg, 0.172 mmol) to yield 52.2 mg (71% yield) of 18 as a pale yellow solid. R$_f$(SiO$_2$/MeOH)=0.64. $^{1H}$ NMR (DMSO-d6): δ 8.95 (s, 1H, Ar—H), 7.95 (s, 1H, Ar—H), 7.87 (d, 2H, Ar—H, J=8.0 Hz), 7.28 (d, 2H, Ar—H, J=8.0 Hz), 5.82 (d, 1H, H-1', J=6.3 Hz), 5.41 (d, 1H, OH, J=6.3 Hz), 5.12 (d, 1H, OH, J=4.6 Hz), 5.04 (t, 1H, OH, J=5.6 Hz), 4.65 (app q, 1H, H-2', $J_{app}$~6.0 Hz), 4.15 (app q, 1H, H-3', $J_{app}$~4.5 Hz), 4.00 (app q, 1H, H-4', $J_{app}$~3.7 Hz), 3.69-3.64 (m, 1H, H-5'), 3.57-3.52 (m, H-5'), 2.34 (s, 3H, CH$_3$). $^{13}$C NMR (DMSO-d$_6$): δ 167.4, 150.9, 150.1, 146.2, 137.6, 137.4, 129.8, 128.2, 125.7, 123.9, 119.5, 87.6, 85.9, 73.6, 71.1, 61.2, 21.3. HRMS calculated for $C_{19}H_{19}N_7O_5Na$ [M+Na]$^+$: 448.1340. found: 448.1342.

Example 22

2-[4-(4-Methoxyphenyl)-1,2,3-triazol-1H-yl]inosine (19)

Step 1: Desilylation.

Using the procedure described for the desilylation of 17, this compound was synthesized from 5 (290.0 mg, 0.351 mmol) and Et$_3$N.3HF (285 μL, 1.75 mmol). Chromatography of the crude reaction mixture on a silica gel column using 10% MeOH in EtOAc yielded 135.0 mg (80% yield) of the O$^6$-allyl-protected nucleoside as a white, foamy solid. R$_f$(SiO$_2$/5% MeOH in EtOAc)=0.19. $^1$H NMR (DMSO-d6): δ 9.32 (s, 1H, Ar—H), 8.75 (s, 1H, Ar—H), 7.95 (d, 2H, Ar—H, J=8.6 Hz), 7.00 (d, 2H, Ar—H, J=8.6 Hz), 6.26-6.18 (m, 1H, =CH), 6.07 (d, 1H, H-1', J=5.7 Hz), 5.56 (dd, 1H, =CH$_{trans}$, J=1.1, 17.2 Hz), 5.37 (dd, 1H, =CH$_{cis}$, J=1.1, 10.4 Hz), 5.28 (d, 2H, OCH$_2$, J=5.5 Hz), 4.63 (t, 1H, H-2', J=5.2 Hz), 4.23 (app t, 1H, H-3', $J_{app}$~4.2 Hz), 4.17 (app q, 1H, H-4', $J_{app}$~3.8), 3.82 (s, 3H, OCH$_3$), 3.70 (dd, 1H, H-5', J=4.2, 12.0 Hz), 3.60 (dd, 1H, H-5', J=4.0, 12.0 Hz).

Step 2: Deallylation.

The desilylated product (94.0 mg, 0.195 mmol) obtained in step 1 was deallylated as described for 17 using Pd(PPh$_3$)$_4$ (11.2 mg, 5 mol %) and PhSO$_2$Na (31.9 mg, 0.195 mmol) to yield 72.1 mg (84% yield) of 19 as a white solid. R$_f$(SiO$_2$/MeOH)=0.73. $^1$H NMR (DMSO-d6): δ 8.94 (s, 1H, Ar—H), 8.01 (s, 1H, Ar—H), 7.99 (d, 2H, Ar—H, J=8.7 Hz), 7.04 (d, 2H, Ar—H, J=8.7 Hz), 5.85 (d, 1H, H-1', J=6.3 Hz), 5.46 (d, 1H, OH, J=6.3 Hz), 5.19 (d, 1H, OH, J=4.6 Hz), 5.11 (t, 1H, OH, J=6.3 Hz), 4.64 (app q, 1H, H-2', $J_{app}$~5.8 Hz), 4.17 (app q, 1H, H-3', $J_{app}$~4.1 Hz), 3.94 (app q, 1H, H-4', $J_{app}$~3.5 Hz), 3.80 (s, 3H, OCH$_3$), 3.71-3.65 (m, 1H, H-5'), 3.59-3.53 (m, 1H, H-5'). $^{13}$C NMR (DMSO-d6): δ 167.1, 159.7, 150.4, 146.2, 137.4, 127.4, 124.9, 124.0, 119.3, 115.0, 94.7, 87.9, 86.2, 73.9, 71.4, 62.5, 55.8. HRMS calculated for $C_{19}H_{19}N_7O_6Na$ [M+Na]$^+$: 464.1289. found: 464.1299.

Example 23

2-[4-(Hydroxymethyl)-1,2,3-triazol-1H-yl]inosine (20)

Step 1: Desilylation.

Using the procedure described for the desilylation of 17, this compound was synthesized from 6 (210.0 mg, 0.280 mmol) and Et$_3$N.3HF (228 μL, 1.40 mmol). Chromatography of the crude reaction mixture on a silica gel column using 10% MeOH in EtOAc yielded 95.0 mg (83% yield) of the O$^6$-allyl-protected nucleoside as a white, foamy solid. R$_f$(SiO$_2$/10% MeOH in EtOAc)=0.46. $^1$H NMR (DMSO-d6): δ 8.77 (s, 1H, Ar—H), 8.74 (s, 1H, Ar—H), 6.24-6.16 (m, 1H, =CH), 6.05 (d, 1H, H-1', J=5.7 Hz), 5.58 (d, 1H, OH, J=5.9 Hz), 5.53 (br d, 1H, =CH$_{trans}$, J=17.2 Hz), 5.39 (d, 1H, OH, J=6.2 Hz), 5.36 (br d, 1H, =CH$_{cis}$, J=10.3 Hz), 5.30 (d, 1H, OH, J=4.9 Hz), 5.24 (d, 2H, OCH$_2$, J=5.9 Hz), 5.04 (t, 1H, OH, J=5.3 Hz), 4.66-4.63 (m, 3H, CH$_2$ and H-2'), 4.22 (app q, 1H, H-3', $J_{app}$~4.5 Hz), 3.99 (app q, 1H, H-4', $J_{app}$~4.0 Hz), 3.73-3.68 (m, 1H, H-5'), 3.62-3.58 (m, 1H, H-5').

Step 2: Deallylation.

The desilylated product (35.2 mg, 0.085 mmol) obtained in step 1 was deallylated as described for 17 using Pd(PPh$_3$)$_4$ (4.9 mg, 5 mol %) and PhSO$_2$Na (14.0 mg, 0.085 mmol) to yield 20.4 mg (64% yield) of 20 as a white solid. R$_f$(SiO$_2$/MeOH)=0.54. $^1$H NMR (DMSO-d$_6$): δ 8.43 (s, 1H, Ar—H), 7.97 (s, 1H, Ar—H), 5.83 (d, 1H, H-1', J=5.8 Hz), 5.42 (d, 1H, OH, J=6.2 Hz), 5.23 (t, 1H, OH, J=5.8 Hz), 5.15 (d, 1H, OH, J=4.8 Hz), 5.06 (t, 1H, OH, J=5.8 Hz), 4.63 (q, 1H, H-2', J=5.9 Hz), 4.58 (d, 2H, CH$_2$, J=5.4 Hz), 4.15 (m, 1H, H-3'), 3.92 (m, 1H, H-4'), 3.67-3.62 (dt, 1H, H-5', J=4.4, 11.7 Hz), 3.56-3.51 (ddd, 1H, H-5', J=4.4, 6.3, 11.2 Hz). $^{13}$C NMR (DMSO-d$_6$): δ 166.9, 150.9, 150.1, 147.8, 137.0, 124.5, 121.4, 87.6, 85.8, 73.6, 71.1, 62.2, 55.4. HRMS calculated for $C_{13}H_{15}N_7O_6Na$ [M+Na]$^+$: 388.0976. found: 388.0982.

Example 24

2-[4-(N-Phthalimidomethyl)-1,2,3-triazol-1H-yl]inosine (21)

Step 1: Desilylation.

Using the procedure described for the desilylation of 17, this compound was synthesized from 7 (350.0 mg, 0.428 mmol) and Et$_3$N.3HF (348 μL, 2.14 mmol). Chromatography of the crude reaction mixture on a silica gel column using 10% MeOH in EtOAc yielded 165.0 mg (72% yield) of the $O^6$-allyl-protected nucleoside as a white, foamy solid. $R_f$(SiO$_2$/EtOAc)=0.23. $^1$H NMR (DMSO-d$_6$): δ 8.90 (s, 1H, Ar—H), 8.73 (s, 1H, Ar—H), 7.93 (dd, 2H, Ar—H, J=3.2, 5.4 Hz), 7.74 (dd, 2H, Ar—H, J=3.2, 5.4 Hz), 6.22-6.14 (m, 1H, =CH), 6.03 (d, 1H, H-1', J=5.8 Hz), 5.56 (d, 1H, OH, J=6.2 Hz), 5.53 (br d, 1H, =CH$_{trans}$, J=17.5 Hz), 5.35 (d, 1H, =CH$_{cis}$, J=10.5 Hz), 5.28 (d, 1H, OH, J=5.0 Hz), 5.22 (d, 2H, OCH$_2$, J=5.6 Hz), 5.02 (t, 1H, OH, J=5.4 Hz), 4.97 (s, 2H, NCH$_2$), 4.62 (app q, 1H, H-2' J$_{app}$~5.5 Hz), 4.20 (app q, 1H, H-3', J$_{app}$~4.5 Hz), 3.98 (app q, 1H, H-4', J$_{app}$~4.1 Hz), 3.71-3.66 (m, 1H, H-5'), 3.60-3.56 (m, 1H, H-5').
Step 2: Deallylation.

The desilylated product (150.0 mg, 0.280 mmol) obtained in step 1 was deallylated as described for 17 using Pd(PPh$_3$)$_4$ (16.2 mg, 5 mol %) and PhSO$_2$Na (45.9 mg, 0.128 mmol) to yield 110.0 mg (79% yield) of 21 as a white solid. $R_f$(SiO$_2$/MeOH)=0.70. $^1$H NMR (DMSO-d6): δ 8.53 (s, 1H, Ar—H), 7.97 (s, 1H, Ar—H), 7.92 (dd, 2H, Ar—H, J=3.2, 5.4 Hz), 7.864 (dd, 2H, Ar—H, J=3.2, 5.4 Hz), 5.80 (d, 1H, H-1', J=6.3 Hz), 5.40 (d, 1H, OH, J=6.3 Hz), 5.13 (d, 1H, OH, J=4.6 Hz), 5.03 (t, 1H, OH, J=5.9 Hz), 4.91 (s, 2H, NCH$_2$), 4.60 (app q, 1H, H-2', J$_{app}$~5.6 Hz), 4.13 (app q, 1H, H-3', J$_{app}$~4.7 Hz), 3.90 (app q, 1H, H-4', J$_{app}$~3.4 Hz), 3.65-3.10 (m, 1H, H-5'), 3.53-3.48 (m, 1H, H-5'). $^{13}$C NMR (DMSO-d6): δ 167.8, 166.3, 150.4, 150.0, 142.2, 137.2, 134.9, 132.1, 124.5, 123.6, 122.1, 87.6, 85.9, 73.7, 71.1, 62.2, 33.3. HRMS calculated for C$_{21}$H$_{19}$N$_8$O$_7$ [M+H]$^+$: 495.1371. found: 495.1379.

Example 25

2-[4-(Ferrocenyl)-1,2,3-triazol-1H-yl]inosine (22)

Step 1: Desilylation.
Using the procedure described for the desilylation of 17, this compound was synthesized from 8 (400.0 mg, 0.442 mmol) and Et$_3$N.3HF (359 μL, 2.21 mmol). Chromatography of the crude reaction mixture on a silica gel column using 10% MeOH in EtOAc yielded 175.0 mg (65% yield) of the $O^6$-allyl-protected nucleoside as a brown, foamy solid. $R_f$(SiO$_2$/5% MeOH in EtOAc)=0.20. $^1$H NMR (DMSO-d$_6$): δ 8.94 (s, 1H, Ar—H), 8.69 (s, 1H, Ar—H), 6.21-6.13 (m, 1H, =CH), 6.02 (d, 1H, H-1', J=5.7 Hz), 5.53 (br s, 1H, OH), 5.52 (br d, 1H, =CH$_{trans}$, J=17.0 Hz), 5.33 (d, 1H, =CH$_{cis}$, J=10.3 Hz), 5.27 (s, 1H, OH), 5.23 (d, 2H, OCH$_2$, J=5.6 Hz), 5.00 (t, 1H, OH, J=4.3 Hz), 4.88 (s, 2H, ferrocenyl-H), 4.60 (br t, 1H, H-2', J=4.5 Hz), 4.33 (s, 2H, ferrocenyl-H), 4.10 (br s, 1H, H-3'), 4.04 (s, 5H, ferrocenyl-H), 3.95 (br s, 1H, H-4'), 3.67-3.65 (m, 1H, H-5'), 3.57-3.55 (m, 1H, H-5').
Step 2: Deallylation.

The desilylated product (95.0 mg, 0.156 mmol) obtained in step 1 was deallylated as described for 17 using Pd(PPh$_3$)$_4$ (9.0 mg, 5 mol %) and PhSO$_2$Na (25.6 mg, 0.156 mmol) to yield 70.1 mg (86% yield) of 22 as a brown red solid. $R_f$(SiO$_2$/MeOH)=0.71. $^1$H NMR (DMSO-d$_6$): δ 8.66 (s, 1H, Ar—H), 7.99 (s, 1H, Ar—H), 5.84 (d, 1H, H-1', J=6.3 Hz), 5.46 (br s, 1H, OH), 5.20 (br s, 1H, OH), 5.09 (t, 1H, OH, J=5.3 Hz), 4.86 (s, 2H, ferrocenyl-H), 4.63 (br s, H-2'), 4.33 (s, 2H, ferrocenyl-H), 4.17 (br s, 1H, H-3'), 4.07 (s, 5H, ferrocenyl-H), 3.94 (br s, 1H, H-4'), 3.69-3.66 (m, 1H, H-5'), 3.57-3.54 (m, 1H, H-5'). $^{13}$C NMR (DMSO-d$_6$): δ 166.9, 150.8, 150.2, 145.2, 137.1, 124.5, 118.9, 87.5, 85.9, 79.6, 76.2, 73.7, 71.2, 69.7, 68.7, 66.8, 62.2. HRMS calculated for C$_{22}$H$_{22}$FeN$_7$O$_5$ [M+H]$^+$: 520.1026. found: 520.1006.

Example 26

2-(4-n-Butyl-1,2,3-triazol-1H-yl)inosine (23)

Step 1: Desilylation.
Using the procedure described for the desilylation of 17, this compound was synthesized from 9 (172.0 mg, 0.222 mmol) and Et$_3$N.3HF (180 μL, 1.10 mmol). Chromatography of the crude reaction mixture on a silica gel column using 10% MeOH in EtOAc yielded 70.1 mg (73% yield) of the $O^6$-allyl-protected nucleoside as a white, foamy solid. $R_f$(SiO$_2$/10% MeOH in EtOAc)=0.57. $^1$H NMR (DMSO-d$_6$): δ 8.73 (s, 1H, Ar—H), 8.69 (s, 1H, Ar—H), 6.23-6.16 (m, 1H, =CH), 6.05 (d, 1H, H-1', J=5.7 Hz), 5.65 (s, 1H, OH), 5.53 (dd, 1H, =CH$_{trans}$, J=1.2, 17.2 Hz), 5.36 (dd, 1H, =CH$_{cis}$, J=1.2, 10.2 Hz), 5.24 (d, 2H, OCH$_2$, J=5.7 Hz), 5.07 (s, 1H, OH), 4.64 (t, 1H, H-2', J=5.0 Hz), 4.23 (t, 1H, H-3', J=3.8 Hz), 4.00 (app q, 1H, H-4', J$_{app}$~4.0 Hz), 3.70 (br d, 1H, H-5', J=10.2 Hz), 3.60 (br d, 1H, H5', J=10.2 Hz), 2.74 (t, 2H, butyl-CH$_2$, J=7.6 Hz), 1.68 (quint, 2H, butyl-CH$_2$, J=7.6 Hz), 1.37 (sextet, 2H, butyl-CH$_2$, J=7.3 Hz), 0.93 (t, 3H, butyl-CH$_3$, J=7.3 Hz). $^{13}$C NMR (DMSO-d$_6$): δ 160.7, 153.2, 148.1, 143.7, 132.8, 121.3, 120.6, 119.5, 87.9, 86.2, 74.2, 70.7, 68.4, 61.6, 31.3, 24.3, 24.8, 22.0, 14.0.
Step 2: Deallylation.

The desilylated product (30.0 mg, 0.069 mmol) obtained in step 1 was deallylated as described for 17 using Pd(PPh$_3$)$_4$ (4.0 mg, 5 mol %) and PhSO$_2$Na (11.4 mg, 0.069 mmol) to yield 19.4 mg (70% yield) of 23 as a white solid. $R_f$(SiO$_2$/MeOH)=0.51. $^1$H NMR (DMSO-d$_6$): δ 8.32 (s, 1H, Ar—H), 7.96 (s, 1H, Ar—H), 5.82 (d, 1H, H-1', J=6.3 Hz), 5.43 (d, 1H$_2$OH, J=6.2 Hz), 5.16 (d, 1H, OH, J=3.9 Hz), 5.07 (t, 1H, OH, J=5.8 Hz), 4.63 (app q, 1H, H-2', J$_{app}$~5.9 Hz), 4.15 (app q, 1H, H-3', J$_{app}$~4.3 Hz), 3.92 (app q, 1H, H-4', J$_{app}$~3.4 Hz), 3.67-3.63 (m, 1H, H-5'), 3.56-3.51 (m, 1H, H-5'), 2.69 (t, 2H, butyl-CH$_2$, J=7.6 Hz), 1.64 (quint, 2H, butyl-CH$_2$, J=7.5 Hz), 1.36 (sextet, 2H, butyl-CH$_2$, J=7.5 Hz), 0.92 (t, 3H, butyl-CH$_3$, J=7.3 Hz). $^{13}$C NMR (DMSO-d$_6$): δ 166.9, 150.9, 150.2, 146.8, 137.1, 124.4, 120.6, 87.6, 85.9, 73.7, 71.1, 62.2, 31.4, 25.0, 22.0, 14.1. HRMS calculated for C$_{16}$H$_{21}$N$_7$O$_5$Na [M+Na]$^+$: 414.1496. found: 414.1499.

Example 27

2-[4-(4-Fluorophenyl)-1,2,3-triazol-1H-yl]inosine (24)

Step 1: Desilylation.
Using the procedure described for the desilylation of 17, this compound was synthesized from 10 (310.0 mg, 0.381 mmol) and Et$_3$N.3HF (310 μL, 1.90 mmol). Chromatography of the crude reaction mixture on a silica gel column using 10% MeOH in EtOAc yielded 143.8 mg (80% yield) of the $O^6$-allyl-protected nucleoside as a white, foamy solid. $R_f$(SiO$_2$/10% MeOH in EtOAc)=0.48. $^1$H NMR (DMSO-d$_6$): δ 9.45 (s, 1H, Ar—H), 8.77 (s, 1H, Ar—H), 8.11 (dd, 2H, Ar—H, J=5.3, 8.6 Hz), 7.36 (t, 2H, Ar—H, J=8.6 Hz), 6.26-6.20 (m, 1H, =CH), 6.18 (d, 1H, H-1', J=5.8 Hz), 5.66 (br s, 1H, OH), 5.57 (dd, 1H, =CH$_{trans}$, J=1.5, 17.2 Hz), 5.43 (br s, 1H, OH), 5.39 (dd, 1H, =CH$_{cis}$, J=1.2, 10.4 Hz), 5.29 (d, 2H, OCH$_2$, J=5.9 Hz), 5.08 (t, 1H, OH, J=4.0 Hz), 4.68 (t, 1H, H-2', J=5.2 Hz), 4.24 (t, 1H, H-3', J=3.9 Hz), 4.01 (app q, 1H, H-4', J$_{app}$~4.0 Hz), 3.74 (dd, 1H, H-5', J=4.2, 11.8 Hz), 3.62 (dd, 1H, H-5', J=3.4, 11.8 Hz).
Step 2: Deallylation.
The desilylated product (24.0 mg, 0.048 mmol) obtained in step 1 was deallylated as described for 17 using Pd(PPh$_3$)$_4$ (2.8 mg, 5 mol %) and PhSO$_2$Na (8.0 mg, 0.048 mmol) to yield 15.0 mg (72% yield) of 24 as a white solid. R$_f$(SiO$_2$/MeOH)=0.42. $^1$H NMR (DMSO-d$_6$): δ 9.12 (s, 1H, Ar—H), 8.05 (s, 1H, Ar—H), 8.03 (br t, 2H, Ar—H, J$_{app}$~6.8 Hz), 7.31 (t, 2H, Ar—H, J=8.5 Hz), 5.87 (d, 1H, H-1', J=6.2 Hz), 5.54 (br d, 1H, OH, J=4.6 Hz), 5.28 (br s, 1H, OH), 5.10 (t, 1H, OH, J=5.5 Hz), 4.66 (br d, 1H, H-2', J=4.5 Hz), 4.18 (br s, 1H, H-3'), 3.94 (br s, 1H, H-4'), 3.69-3.66 (m, 1H, H-5'), 3.57-3.54 (m, 1H, H-5'). $^{13}$C NMR (DMSO-d$_6$): δ 167.1, 163.2 and 161.3 (d, $^1$J=244.6 Hz), 150.8, 150.2, 145.2, 137.4, 127.9 and 127.8 (d, $^3$J=8.2 Hz), 127.6, 124.5, 120.0, 116.3 and 116.1 (d, $^2$J=21.5 Hz), 87.6, 86.0, 73.7, 71.1, 62.2. HRMS calculated for C$_{18}$H$_{16}$FN$_7$O$_5$Na [M+Na]$^+$: 452.1089. found: 452.1090.

Example 28

2-[4-(Phenyl)-1,2,3-triazol-1H-yl]-2'-deoxyinosine (25)

Step 1: Desilylation.

Using the procedure described for the desilylation of 17, this compound was synthesized from 11 (230.0 mg, 0.346 mmol) and Et$_3$N.3HF (187 FAL, 1.15 mmol). Chromatography of the crude reaction mixture on a silica gel column using 8% MeOH in EtOAc yielded 120.1 mg (76% yield) of the O$^6$-allyl-protected nucleoside as a white, foamy solid. R$_f$(SiO$_2$/10% MeOH in EtOAc)=0.50. $^1$H NMR (DMSO-d6): δ 9.44 (s, 1H, Ar—H), 8.72 (s, 1H, Ar—H), 8.07 (d, 2H, Ar—H, J=7.8 Hz), 7.51 (t, 2H, Ar—H, J=7.5 Hz), 7.41 (t, 1H, Ar—H, J=7.5 Hz), 6.51 (t, 1H, H-1', J=6.4 Hz), 6.26-6.18 (m, 1H, =CH), 5.56 (br d, 1H, =CH$_{trans}$, J=17.2 Hz), 5.38 (br d, 1H, =CH$_{cis}$, J=10.4 Hz), 5.28 (d, 2H, OCH$_2$, J=5.9 Hz), 4.49 (br s, 1H, H-3'), 3.91 (br d, 1H, H-4', J=2.5 Hz), 3.67 (dd, 1H, H-5', J=4.5, 11.8 Hz), 3.57 (dd, 1H, H-5', J=4.3, 11.8 Hz), 2.79 (app quint, 1H, H-2', J$_{app}$~6.5 Hz), 2.39 (ddd, 1H, H-2', J=2.5, 6.0, 9.5 Hz). $^{13}$C NMR (DMSO-d$_6$): δ 160.7, 152.9, 147.9, 147.2, 143.8, 132.9, 130.3, 129.4, 128.9, 126.0, 120.8, 120.7, 119.7, 88.6, 84.2, 71.1, 68.6, 61.9, 40.2.

Step 2: Deallylation.

The desilylated product (95.0 mg, 0.218 mmol) obtained in step 1 was deallylated as described for 17 using Pd(PPh$_3$)$_4$ (12.6 mg, 5 mol %) and PhSO$_2$Na (35.7 mg, 0.218 mmol) to yield 64.3 mg (75% yield) of 25 as a white solid. R$_f$(SiO$_2$/MeOH)=0.54. $^1$H NMR (DMSO-d6): δ 9.06 (s, 1H, Ar—H), 8.00 (s, 1H, Ar—H), 7.98 (d, 2H, Ar—H, J=7.6 Hz), 7.46 (t, 2H, Ar—H, J=7.5 Hz), 7.36 (t, 1H, Ar—H, J=7.1 Hz), 6.31 (t, 1H, H-1', J=6.7 Hz), 5.30 (br s, 1H, OH), 4.97 (br s, 1H, OH), 4.42 (br s, 1H, H-3'), 3.85 (br s, 1H, H-4'), 3.63-3.60 (m, 1H, H-5'), 3.55-3.50 (m, 1H, H-5'), 2.72 (app quint, 1H, H-2', J$_{app}$~6.6 Hz), 2.24 (br dd, 1H, H-2', J=3.0, 11.3 Hz). $^{13}$C NMR (DMSO-d6): δ 166.8, 150.8, 149.9, 146.0, 136.7, 131.1, 129.3, 128.3, 125.8, 121.5, 120.0, 88.1, 83.6, 71.5, 62.4, 40.1. HRMS calculated for C$_{18}$H$_{17}$N$_7$O$_4$Na [M+Na]$^+$: 418.1234. found: 418.1240.

Example 29

2-[4-(4-Methoxyphenyl)-1,2,3-triazol-1H-yl]-2'-deoxyinosine (26)

Step 1: Desilylation.

Using the procedure described for the desilylation of 17, this compound was synthesized from 12 (171.0 mg, 0.24 mmol) and Et$_3$N.3HF (133 µL, 0.821 mmol). Chromatography of the crude reaction mixture on a silica gel column using 10% MeOH in EtOAc yielded 104.1 mg (93% yield) of the O$^6$-allyl-protected nucleoside as a white, foamy solid. R$_f$(SiO$_2$/10% MeOH in EtOAc)=0.38. $^1$H NMR (DMSO-d$_6$): δ 9.33 (s, 1H, Ar—H) 8.72 (s, 1H, Ar—H), 7.99 (d, 2H, Ar—H, J=8.6 Hz), 7.07 (d, 2H, Ar—H, J=8.6 Hz), 6.48 (t, 1H, H-1', J=6.7 Hz), 6.26-6.18 (m, 1H, =CH), 5.56 (d, 1H, =CH$_{trans}$, J=17.4 Hz), 5.42 (d, 1H, OH, J=4.0 Hz), 5.38 (d, 1H, =CH$_{cis}$, J=10.5 Hz), 5.28 (d, 2H, OCH$_2$, J=5.6 Hz), 4.96 (t, 1H, OH, J=5.4 Hz), 4.49 (br s, 1H, H-3'), 3.92 (br d, 1H, H-4', J=2.9 Hz), 3.82 (s, 3H, OCH$_3$), 3.68-3.64 (m, 1H, H-5'), 3.60-3.55 (m, 1H, H-5'), 2.80 (app quint, 1H, H2', J$_{app}$~7.0 Hz), 2.40 (ddd, 1H, H-2', J=3.0, 6.5, 10.5 Hz).

Step 2: Deallylation.

The desilylated product (100.0 mg, 0.214 mmol) obtained in step 1 was deallylated as described for 17 using Pd(PPh$_3$)$_4$ (12.4 mg, 5 mol %) and PhSO$_2$Na (35.1 mg, 0.048 mmol) to yield 78.1 mg (80% yield) of 26 as a pale yellow solid. R$_f$(SiO$_2$/MeOH)=0.46. $^{1H}$ NMR (DMSO-d$_6$): δ 8.97 (s, 1H, Ar—H), 8.02 (s, 1H, Ar—H), 7.91 (d, 2H, Ar—H, J=8.1 Hz), 7.03 (d, 2H, Ar—H, J=8.1 Hz), 6.32 (t, 1H, H-1', J=6.6 Hz), 5.30 (br s, 1H, OH), 4.99 (br s, 1H, OH), 4.43 (br s, 1H, H-3'), 3.86 (br s, 1H, H-4'), 3.80 (s, 3H, OCH$_3$), 3.63-3.61 (m, 1H, H-5'), 3.54-3.52 (m, 1H, H-5'), 2.73 (app quint, 1H, H-2', J$_{app}$~6.6 Hz), 2.25 (br dd, 1H, H-2', J=5.5, 11.5 Hz). $^{13}$C NMR (DMSO-d$_6$): δ 166.9, 159.4, 150.9, 149.9, 145.9, 139.6, 127.1, 124.4, 123.7, 119.0, 114.7, 88.1, 83.5, 71.5, 62.4, 55.6, 40.1. HRMS calculated for C$_{19}$H$_{19}$N$_7$O$_5$Na [M+Na]$^+$: 448.1340. found: 448.1346.

Example 30

2-[4-(Hydroxymethyl)-1,2,3-triazol-1H-yl]-2'-deoxyinosine (27)

Step 1: Desilylation.

Using the procedure described for the desilylation of 17, this compound was synthesized from 13 (211.0 mg, 0.341 mmol) and Et$_3$N.3HF (183 µL, 1.13 mmol). Chromatography of the crude reaction mixture on a silica gel column using 15% MeOH in EtOAc yielded 103.5 mg (78% yield) of the O$^6$-allyl-protected nucleoside as a white, foamy solid. R$_f$(SiO$_2$/10% MeOH in EtOAc)=0.33. $^{1H}$ NMR (DMSO-d6): δ 8.77 (s, 1H, Ar—H), 8.70 (s, 1H, Ar—H), 6.48 (t, 1H, H-J=6.8 Hz), 6.23-6.15 (m, 1H, =CH), 5.53 (br d, 1H, =CH$_{trans}$, J=17.3 Hz), 5.38 (d, 1H, OH, J=4.2 Hz), 5.35 (br d, 1H, =CH$_{cis}$, J=10.6 Hz), 5.36 (t, 1H, OH, J=5.6 Hz), 5.22 (d, 2H, OCH$_2$, J=5.9 Hz), 4.92 (t, 1H, OH, J=5.6 Hz), 4.64 (d, 2H, CH$_2$, J=5.6 Hz), 4.46 (m, 1H, H-3'), 3.91 (app q, 1H, H-4', J$_{app}$~3.2 Hz), 3.65-3.61 (m, 1H, H-5'), 3.57-3.52 (m, 1H, H-5'), 2.78 (app sextet, 1H, H-2', J$_{app}$~6.5 Hz), 2.40 (ddd, 1H, H-2', J=3.7, 6.3, 10.0 Hz).

Step 2: Deallylation.

The desilylated product (82.0 mg, 0.210 mmol) obtained in step 1 was deallylated as described for 17 using Pd(PPh$_3$)$_4$ (12.1 mg, 5 mol %) and PhSO$_2$Na (34.4 mg, 0.210 mmol) to yield 65.0 mg (88% yield) of 27 as a pale yellow solid. R$_f$(SiO$_2$/MeOH)=0.50. $^{1H}$ NMR (DMSO-d6): δ 8.44 (s, 1H, Ar—H), 7.98 (s, 1H, Ar—H), 6.28 (t, 1H, H-1', J=6.4 Hz), 5.30 (d, 1H, OH, J=3.4 Hz), 5.24 (t, 1H, OH, J=5.7 Hz), 4.96 (t, 1H, OH, J=5.4 Hz), 4.58 (d, 2H, CH$_2$, J=5.0 Hz), 4.40 (br s, 1H, H-3'), 3.84 (br s, 1H, H-4'), 3.61-3.58 (m, 1H, H-5'), 3.52-3.50 (m, 1H, H-5'), 2.70 (app quint, 1H, H-2', J$_{app}$~5.5 Hz), 2.22 (br dd, 1H, H-2', J=3.0, 12.7 Hz). $^{13}$C NMR (DMSO-d6): δ 166.5, 150.6, 149.9, 147.8, 136.8, 124.3, 121.5, 88.1, 83.5, 71.4, 62.4, 55.4, 40.1. HRMS calculated for C$_{13}$H$_{15}$N$_7$O$_5$Na [M+Na]$^+$: 372.1027. found: 372.1029.

Example 31

2-[4-(N-Phthalimidomethyl)-1,2,3-triazol-1H-yl]-2'-deoxyinosine (28)

Step 1: Desilylation.

Using the procedure described for the desilylation of 17, this compound was synthesized from 14 (289.0 mg, 0.387 mmol) and Et$_3$N.3HF (201 µL, 1.29 mmol). Chromatography of the crude reaction mixture on a silica gel column using 10% MeOH in EtOAc yielded 159.3 mg (79% yield) of the O$^6$-allyl-protected nucleoside as a yellow, foamy solid. R$_f$(SiO$_2$/10% MeOH in EtOAc)=0.56. $^1$H NMR (DMSO-d$_6$): δ 8.91 (s, 1H, Ar—H), 8.70 (s, 1H, Ar—H), 7.93 (br d, 2H, Ar—H, J=3.6 Hz), 7.88 (br d, 2H, Ar—H, J=3.6 Hz), 6.46 (t, 1H, H-1', J=6.7 Hz), 6.21-6.13 (m, 1H, =CH), 5.52 (d, 1H, =CH$_{trans}$, J=16.5 Hz), 5.38 (d, 1H, OH, J=4.0 Hz), 5.34 (d, 1H, =CH$_{cis}$, J=10.6 Hz), 5.20 (d, 2H, OCH$_2$, J=5.6 Hz), 4.97 (s, 2H, NCH$_2$), 4.92 (t, 1H, OH, J=5.4 Hz), 4.45 (br s, 1H, H-3'), 3.89 (br d, 1H, H-4', J=2.8 Hz), 3.64-3.60 (m, 1H, H-5'), 3.56-3.52 (m, 1H, H-5'), 2.80 (app quint, 1H, H-2', J$_{app}$~6.5 Hz), 2.36 (ddd, 1H, H-2', J=3.4, 6.0, 9.6 Hz).

Step 2: Deallylation.

The desilylated product (144.0 mg, 0.277 mmol) obtained in step 1 was deallylated as described for 17 using Pd(PPh$_3$)$_4$ (16.0 mg, 5 mol %) and PhSO$_2$Na (45.4 mg, 0.277 mmol) to yield 98.9 mg (75% yield) of 28 as a pale yellow solid. R$_f$(SiO$_2$/MeOH)=0.49. $^1H$ NMR (DMSO-d$_6$): δ 8.54 (s, 1H, Ar—H), 7.97 (s, 1H, Ar—H), 7.92 (dd, 2H, Ar—H, J=3.0, 5.4 Hz), 7.86 (dd, 2H, Ar—H, J=3.0, 5.4 Hz), 6.26 (t, 1H, H-1', J=6.2 Hz), 5.32 (d, 1H, OH, J=4.0 Hz), 4.94 (t, 1H, OH, J=5.7 Hz), 4.81 (s, 2H, NCH$_2$), 4.38 (br s, 1H, H-3'), 3.85 (app q, 1H, H-4', J$_{app}$~4.5 Hz), 3.60-3.57 (m, 1H, H-5'), 3.56-3.48 (m, 1H, H-5'), 2.70 (app quint, 1H, H-2', J$_{app}$~5.5 Hz), 2.38 (ddd, 1H, H-2', J=2.5, 5.2, 11.0 Hz). $^{13}$C NMR (DMSO-d$_6$): δ 167.8, 166.6, 150.6, 149.8, 142.2, 136.7, 134.9, 132.1, 124.4, 123.6, 122.1, 88.1, 83.5, 71.4, 62.4, 40.2, 33.3. HRMS calculated for C$_{21}$H$_{18}$N$_8$O$_6$Na [M+Na]$^+$: 501.1242. found: 501.1241.

Example 32

2-[4-(Ferrocenyl)-1,2,3-triazol-1H-yl]-2'-deoxyinosine (29)

Step 1: Desilylation.

Using the procedure described for the desilylation of 17, this compound was synthesized from 15 (394.0 mg, 0.480 mmol) and Et$_3$N.3HF (257 µL, 1.60 mmol). Chromatography of the crude reaction mixture on a silica gel column using 10% MeOH in EtOAc yielded 240.8 mg (84% yield) of the O$^6$-allyl-protected nucleoside as a brown, foamy solid. R$_f$(SiO$_2$/10% MeOH in EtOAc)=0.58. $^1$H NMR (DMSO-d$_6$): δ 9.00 (s, 1H, A-H) 8.71 (s, 1H, Ar—H), 6.51 (t, 1H, H-1', J=6.7 Hz), 6.26-6.18 (m, 1H, =CH), 5.57 (dd, 1H, =CH$_{trans}$, J=1.5, 17.2 Hz), 5.42 (d, 1H, OH, J=4.0 Hz), 5.34 (br d, 1H, =CH$_{cis}$, J=11.2 Hz), 5.28 (d, 2H, OCH$_2$, J=5.6 Hz), 4.96 (t, 1H, OH, J=5.5 Hz), 4.94 (s, 2H, ferrocenyl-H), 4.49 (br s, 1H, H-3'), 4.39 (s, 2H, ferrocenyl-H), 4.10 (s, 5H, ferrocenyl-H), 3.92 (br d, 1H, H-4', J=3.0 Hz), 3.68-3.64 (m, 1H, H-5'), 3.60-3.56 (m, 1H, H-5'), 2.78 (app quint, 1H, H2', J$_{app}$~6.5 Hz), 2.40 (ddd, 1H, H-2', J=3.5, 6.5, 9.5 Hz).

Step 2: Deallylation.

The desilylated product (189.0 mg, 0.319 mmol) obtained in step 1 was deallylated as described for 17 using Pd(PPh$_3$)$_4$ (18.4 mg, 5 mol %) and PhSO$_2$Na (52.3 mg, 0.319 mmol) to yield 135.1 mg (84% yield) of 29 as a brownish red solid. R$_f$(SiO$_2$/MeOH)=0.53. $^1H$ NMR (DMSO-d$_6$): δ 8.65 (s, 1H, Ar—H), 7.98 (s, 1H, Ar—H), 6.51 (t, 1H, H-1', J=6.2 Hz), 5.32 (d, 1H, OH, J=3.9 Hz), 4.98 (t, 1H, OH, J=5.7 Hz), 4.86 (s, 2H, ferrocenyl-H), 4.42 (br s, 1H, H-3'), 4.34 (s, 2H, ferrocenyl-H), 4.07 (s, 5H, ferrocenyl-H), 3.86 (br d, 1H, H-4', J=2.3 Hz), 3.64-3.60 (m, 1H, H-5'), 3.56-3.51 (m, 1H, H-5'), 2.71 (app quint, 1H, H-2', J$_{app}$~6.6 Hz), 2.24 (ddd, 1H, H2', J=2.0, 6.0. 10.9 Hz). $^{13}$C NMR (DMSO-d$_6$): δ 166.6, 150.7, 149.9, 145.2, 136.5, 131.9, 129.1, 118.9, 88.1, 83.5, 76.2, 71.5, 69.6, 68.7, 66.8, 62.4, 40.2. HRMS calculated for C$_{22}$H$_{21}$FeN$_7$O$_4$Na [M+Na]$^+$: 526.0897. found: 526.0890.

Example 33

2-(4-n-Butyl-1,2,3-triazol-1H-yl)-2'-deoxyinosine (30)

Step 1: Desilylation.

Using the procedure described for the desilylation of 17, this compound was synthesized from 16 (275.1 mg, 0.427 mmol) and Et$_3$N.3HF (231 µL, 1.42 mmol). Chromatography of the crude reaction mixture on a silica gel column using 8% MeOH in EtOAc yielded 152.3 mg (86% yield) of the O$^6$-allyl-protected nucleoside as a brown, foamy solid. R$_f$(SiO$_2$/10% MeOH in EtOAc)=0.50. $^1$H NMR (DMSO-d$_6$): δ 8.70 (s, 2H, Ar—H), 6.48 (t, 1H, H-1', J=6.6 Hz), 6.24-6.16 (m, 1H, =CH), 5.54 (d, 1H, =CH$_{trans}$, J=17.2 Hz), 5.39 (br s, 1H, OH), 5.36 (d, 1H, =CH$_{cis}$, J=10.6 Hz), 5.22 (d, 2H, OCH$_2$, J=5.4 Hz), 4.93 (br s, 1H, OH), 4.48 (br s, 1H, H-3'), 3.91 (br d, 1H, H-4', J=2.7 Hz), 3.65 (br d, 1H, H-5', J=10.5 Hz), 3.57 (br d, 1H, H-5', J=10.5 Hz), 2.80-2.73 (m, 3H, butyl-CH$_2$, and H-2') 2.38 (br dd, 1H, H-2', J=3.4, 7.5 Hz), 1.69 (quint, 2H, butyl-CH$_2$, J=7.5 Hz), 1.39 (sextet, 2H, butyl-CH$_2$, J=7.5 Hz), 0.94 (t, 3H, butyl-CH$_3$, J=7.3 Hz).

Step 2: Dealtylation.

The desilylated product (144.0 mg, 0.346 mmol) obtained in step 1 was deallylated as described for 17 using Pd(PPh$_3$)$_4$ (20.0 mg, 5 mol %) and PhSO$_2$Na (56.7 mg, 0.346 mmol) to yield 89.3 mg (69% yield) of 30 as white solid. R$_f$(SiO$_2$/MeOH)=0.55. $^1$H NMR (DMSO-d$_6$): δ 8.35 (s, 1H, Ar—H), 8.00 (s, 1H, Ar—H), 6.28 (t, 1H, H-1', J=6.3 Hz), 5.32 (br s, 1H, OH), 4.98 (br s, 1H, OH), 4.41 (br s, 1H, H-3'), 3.85 (br s, 1H, H-4'), 3.61-3.59 (m, 1H, H-5'), 3.52-3.50 (m, 1H, H-5'), 2.73-2.65 (m, 3H, butyl-CH$_2$, and H-2'), 2.38 (ddd, 1H, H-2', J=3.5, 8.5, 11.0 Hz), 1.63 (quint, 2H, butyl-CH$_2$, J=7.4 Hz), 1.35 (sextet, 2H, butyl-CH$_2$, J=7.4 Hz), 0.91 (t, 3H, butyl-CH$_3$, J=7.3 Hz). $^{13}$C NMR (DMSO-d$_6$): δ 166.9, 150.8, 149.9, 146.8, 136.7, 124.2, 120.6, 88.1, 83.5, 71.5, 62.4, 40.1, 31.4, 25.0, 22.1, 14.1. HRMS calculated for C$_{16}$H$_{21}$N$_7$O$_4$Na [M+Na]$^+$: 398.1547. found: 398.1553.

Example 34

O$^6$-(1-Benzotriazol-1H-yl)-2-(4-phenyl-1,2,3-triazol-1H-yl)-2',3',5'-tri-O-(tert-butyldimethylsilyl)inosine (31)

Step 1: Dealtylation.

Following the procedure described for the preparation of 17, compound 3 (170 mg, 0.214 mmol) was deallylated using Pd(PPh$_3$)$_4$ (12.3 mg, 5 mol %) and PhSO$_2$Na (35.1 mg, 0.214 mmol). Chromatographic purification of the crude material on a silica gel column using 10% MeOH in EtOAc afforded 146.3 mg (91% yield) of the deallylated compound as a clear gum. R$_f$(SiO$_2$/10% MeOH in EtOAc)=0.46. $^1$H NMR (DMSO-d$_6$): δ 8.96 (s, 1H, Ar—H), 8.05 (s, 1H, Ar—H), 7.95 (d, 2H, Ar—H, J=7.6 Hz), 7.47 (t, 2H, Ar—H, J=7.2 Hz), 7.36

(t, 1H, Ar—H, J=7.2 Hz), 5.85 (d, 1H, H-1', J=6.4 Hz), 5.12 (t, 1H, H-2', J=5.0 Hz), 4.30 (br s, 1H, H-3'), 4.08 (dd, 1H, H-5', J=6.9, 10.8 Hz), 3.97 (br s, 1H, H-4'), 3.72 (dd, 1H, H-5', J=3.5, 10.8 Hz), 0.92, 0.86, and 0.72 (3s, 27H, t-Bu), 0.14, 0.12, 0.07, 0.05, −0.10, and −0.31 (6s, 18H, SiCH$_3$).

Step 2: Introduction of the O$^6$-Benzotriazolyl Group.

In a clean, dry round-bottomed flask equipped with a stifling bar were placed the 2-[(4-phenyl)-1,2,3-triazol-1H-yl]-2',3'-5'-tri-O-(tert-butyldimethylsilyl)inosine derivative 3 (160.0 mg, 0.212 mmol), BOP (187.7 mg, 0.424 mmol), and i-Pr2NEt (45 μL, 0.318 mmol) in dry THF (4.0 mL). The reaction mixture was flushed with nitrogen gas, and stirred at room temperature for 24 h, at which time TLC indicated complete reaction. The mixture was diluted with EtOAc and washed with water containing a small amount of NaCl, the aqueous layer was separated and reextracted with EtOAc. The combined organic layer was dried over Na$_2$SO$_4$ and evaporated to dryness. Chromatographic purification of the crude material on a silica gel column using 20% EtOAc in hexanes provided 101.4 mg (55% yield) of 31 as a white foam. R$_f$(SiO$_2$/20% EtOAc in hexanes)=0.57. $^1$H NMR (CDCl$_3$): δ 8.75 (s, 1H, Ar—H), 8.21 (d, 1H, Ar—H, J=8.4 Hz), 7.87 (s, 1H, Ar—H), 7.74 (d, 2H, Ar—H, J=7.3 Hz), 7.59-7.49 (m, 3H, Ar—H), 7.40 (t, 2H, Ar—H, J=7.4 Hz), 7.33 (t, 1H, Ar—H, J=7.4 Hz), 6.21 (d, 1H, H-1', J=3.7 Hz), 4.61 (t, 1H, H-2', J=3.9 Hz), 4.37 (t, 1H, H-3', J=4.6 Hz), 4.22 (app q, 1H, H-4', J$_{app}$~3.6 Hz), 4.14 (dd, 1H, H-5', J=3.6, 11.6 Hz), 3.85 (dd, 1H, H-5', J=2.5, 11.6 Hz), 0.98, 0.93, and 0.85 (3s, 27H, t-Bu), 0.19, 0.17, 0.12, 0.09, 0.06, and 0.02 (6s, 18H, SiCH$_3$). $^{13}$C NMR (CDCl$_3$): δ159.7, 155.1, 147.9, 147.8, 145.4, 143.6, 129.8, 129.4, 129.2, 129.0, 128.8, 126.1, 125.3, 120.9, 119.4, 118.5, 108.8, 89.7, 85.4, 76.6, 71.2, 62.1, 26.3, 26.0, 25.9, 18.8, 18.3, 18.1, −4.1, −4.6, −5.1, −5.2. FIRMS calculated for C$_{42}$H$_{63}$N$_{10}$O$_5$Si$_3$ [M+H]$^+$: 871.4285. found: 871.4298.

Example 35

6-(Morpholin-4-yl)-2-(4-phenyl-1,2,3-triazol-1H-yl)-9-[2',3',5'-tri-O-(tert-butyldimethylsilyl)-β-D-ribofuranosyl]purine (32)

In a clean, dry reaction vial equipped with a stirring bar was placed 31 (50.0 mg, 0.057 mmol) in dry DME (2 mL). Morpholine (20.0 μL, 0.229 mmol) was added, the reaction mixture was flushed with nitrogen gas, and allowed to stir at room temperature for 1 h. The reaction mixture was evaporated, the residue was dissolved in EtOAc and washed with water containing a small amount of NaCl. The aqueous layer was separated and reextracted with EtOAc. The combined organic layer was dried over Na$_2$SO$_4$ and evaporated to dryness. Chromatographic purification of the crude material on a silica gel column using 20% EtOAc in hexanes afforded 36.1 mg (77% yield) of 32 as a white foam. R$_f$(SiO$_2$/30% EtOAc in hexanes)=0.70. $^1$H NMR (CDCl$_3$): δ 8.69 (s, 1H, Ar—H), 8.20 (s, 1H, Ar—H), 7.95 (d, 2H, Ar—H, J=7.2 Hz), 7.46 (t, 2H, Ar—H, J=7.5 Hz), 7.36 (t, 1H, Ar—H, J=7.5 Hz), 6.11 (d, 1H, H-1', J=4.5 Hz), 4.60 (t, 1H, H-2', J=4.5 Hz), 4.48-4.35 (br m, 4H, 2CH$_2$), 4.34 (t, 1H, H-3', J=4.3 Hz), 4.15 (app q, 1H, H-4', J$_{app}$~3.6 Hz), 4.08 (dd, 1H, H-5', J=3.7, 11.4 Hz), 3.88 (t, 4H, 2CH$_2$, J=4.8 Hz), 3.82 (dd, 1H, H-5', J=2.8, 11.4 Hz), 0.96, 0.94, and 0.88 (3s, 27H, t-Bu), 0.16, 0.14, 0.12, 0.10, 0.01, and −0.06 (6s, 18H, SiCH$_3$). $^{13}$C NMR (CDCl$_3$): δ 153.8, 151.3, 149.0, 147.2, 138.3, 130.4, 128.8, 128.2, 125.9, 119.5, 118.4, 88.3, 85.0, 75.9, 71.5, 66.9, 62.3, 45.8 (br s), 26.1, 25.8, 25.6, 18.5, 18.0, 17.8, −4.3, −4.7, −5.3. HRMS calculated for C$_{40}$H$_{67}$N$_8$O$_5$Si$_3$ [M+H]$^+$: 823.4537. found: 823.4550.

Example 36

6-(N-Benzyl)-2-(4-phenyl-1,2,3-triazol-1H-yl)-2',3',5'-tri-O-(tert-butyldimethylsilyl)adenosine (33)

As described for the synthesis of 32, this compound was prepared by a reaction between 31 (50.0 mg, 0.057 mmol) and benzylamine (25.0 μL, 0.228 mmol) in dry DME (2.0 mL) at room temperature over 10 h. Workup as described for 32 and chromatographic purification of the crude material on a silica gel column using 20% EtOAc in hexanes afforded 43.1 mg (90% yield) of 33 as a white foam. R$_f$(30% EtOAc in hexanes)=0.55. $^1$H NMR (CDCl$_3$): δ 8.68 (s, 1H, Ar—H), 8.41 (br s, 1H, Ar—H), 7.95 (d, 2H, Ar—H, J=7.8 Hz), 7.48-7.45 (m, 4H, Ar—H Hz), 7.38-7.34 (m, 3H, Ar—H), 7.28 (app t, 1H, Ar—H, J=7.3 Hz), 6.90 (br s, 1H, NH), 6.10 (d, 1H, H-1', J=3.8 Hz), 4.93 (br s, 2H, CH$_2$), 4.58 (t, 1H, H-2', J=3.9 Hz), 4.34 (t, 1H, H-3', J=4.6 Hz), 4.17 (br s, 1H, H-4'), 4.12 (br d, 1H, H-5', J=11.0 Hz), 3.83 (dd, 1H, H-5', J=2.0, 11.0 Hz), 0.97, 0.92, and 0.86 (3s, 27H, t-Bu), 0.17, 0.15, 0.11, 0.09, 0.05, and 0.02 (6s, 18H, SiCH$_3$). $^{13}$C NMR (CDCl$_3$): δ 154.3, 150.3, 148.8, 147.4, 138.5, 137.7, 130.4, 128.9, 128.8, 128.4, 128.1, 127.8, 126.0, 118.7, 89.3, 84.3, 76.2, 70.6, 61.8, 60.4, 45.2, 26.2, 25.9, 25.8, 18.6, 18.1, 18.0, −4.1, −4.4, −4.7, −5.1, −5.3. HRMS calculated for C$_{43}$H$_{67}$N$_8$O$_4$Si$_3$ [M+H]$^+$: 843.4588. found: 843.4596.

Example 37

6-(Morpholin-4-yl)-2-(4-phenyl-1,2,3-triazol-1H-yl)-9-(β-D-ribofuranosyl)purine (34)

Using the procedure described for the desilylation of 17, this compound was synthesized from 32 (30.0 mg, 0.036 mmol) and Et$_3$N.3HF (29.0 μL, 0.18 mmol). Chromatography of the crude reaction mixture on a silica gel column using 10% MeOH in EtOAc yielded 13.9 mg (80% yield) of 34 as a white, foamy solid. R$_f$(SiO$_2$/30% MeOH in EtOAc)=0.57. $^1$H NMR (DMSO-d$_6$): δ 9.34 (s, 1H, Ar—H), 8.55 (s, 1H, Ar—H), 8.05 (d, 2H, Ar—H, J=7.8 Hz), 7.50 (t, 2H, Ar—H, J=7.5 Hz), 7.39 (t, 1H, Ar—H, J=7.5 Hz), 6.03 (d, 1H, H-1', J=5.8 Hz), 5.53 (d, 1H, OH, J=6.0 Hz), 5.27 (d, 1H, OH, J=4.9 Hz), 5.01 (t, 1H, OH, J=5.6 Hz), 4.64 (app quint, 1H, H-2', J$_{app}$~5.8 Hz), 4.48-4.35 (br m, 4H, 2CH$_2$), 4.22 (app q, 1H, H-3', J$_{app}$~4.8 Hz), 3.98 (app q, 1H, H-4', J=3.8 Hz), 3.80 (t, 4H, 2CH$_2$, J=4.8 Hz), 3.79-3.70 (m, 1H, H-5'), 3.62-3.58 (m, 1H, H-5'). $^{13}$C NMR (DMSO-d$_6$): δ 153.7, 151.8, 148.8, 146.9, 140.2, 130.5, 129.3, 128.3, 126.0, 120.5, 119.2, 87.7, 86.2, 74.2, 70.8, 66.6, 61.8, 46.0 (br s). HRMS calculated for C$_{22}$H$_{24}$N$_8$O$_5$Na [M+Na]$^+$: 503.1762. found: 503.1765.

Example 38

6-(N-Benzyl)-2-[4-(phenyl)-1,2,3-triazol-1H-yl]adenosine (35)

Using the procedure described for the desilylation of 17, this compound was synthesized from 33 (35.0 mg, 0.041 mmol) and Et$_3$N.3HF (34.0 μL, 0.207 mmol). Chromatography of the crude reaction mixture on a silica gel column using 10% MeOH in EtOAc yielded 16.8 mg (82% yield) of 35 as a white, foamy solid. R$_f$(SiO$_2$/30% MeOH in EtOAc)=0.44. $^1$H NMR (DMSO-d$_6$): δ 9.22 (s, 1H, Ar—H), 9.04 (br s, 1H, NH), 8.51 (s, 1H, Ar—H), 8.02 (d, 2H, Ar—H, J=7.6 Hz), 7.50 (m, 4H, Ar—H), 7.39 (t, 1H, Ar—H, J=7.3 Hz), 7.33 (t, 2H, Ar—H, J=7.5 Hz), 7.23 (t, 1H, Ar—H, J=7.3 Hz), 6.00 (d, 1H, H-1', J=6.0 Hz), 5.51 (d, 1H, OH, J=5.6 Hz), 5.25 (d, 1H, OH, J=3.9 Hz), 5.00 (t, 1H, OH, J=5.8 Hz), 4.81-4.90 (m, 2H, CH$_2$), 4.69-4.62 (m, 1H, H-2'), 4.28-4.24 (m, 1H, H-3'), 4.17 (m, 1H, H-4'), 3.72-3.70 (m, 1H, H-5'), 3.62-3.58 (m, 1H, H-5'). $^{13}$C NMR (DMSO-d$_6$): δ 155.1, 151.3, 149.8, 149.3, 146.8, 141.1, 140.0, 130.5, 129.3, 128.7, 128.1, 127.3, 126.0, 120.3, 119.4, 87.6, 86.2, 74.1, 70.9, 61.9, 43.8. HRMS calculated for C$_{25}$H$_{24}$N$_8$O$_4$Na [M+Na]$^+$: 523.1813. found: 523.1822.

Example 39

2-Azido-O$^6$-(benzotriazol-1H-yl)-2',3',5'-tri-O-(tert-butyldimethylsilyl)inosine (38)

A solution of 37 (50.0 mg, 0.067 mmol) in CH$_2$Cl$_2$ (3 mL) was cooled to 78° C. To this stirred solution TMS—N3 (0.088 mL, 0.67 mmol) was added followed by dropwise addition of t-BuONO (0.08 mL, 0.67 mmol). The reaction mixture was allowed to warm to rt and stirred for 9 h. To the reaction mixture were added 1:1 H$_2$O/MeOH (1 mL) and the stifling was continued for 1 h. The mixture was then extracted with CH$_2$Cl$_2$. After layer separation, the organic layer was removed, washed with water, dried over Na$_2$SO$_4$ and evaporated to dryness. The crude product was purified on silica gel column using 10% EtOAc/hexanes to afford 25.5 mg (49% yield) of 38 as white, foamy solid. R$_f$ (SiO$_2$/30% EtOAc in hexanes)=0.66. IR (neat): 2955, 2930, 2857, 2128, 1618, 1570 cm$^{-1}$. The following $^1$H and $^{13}$C NMR data list all discernible signals of the isomer mixture. $^1$H NMR (500 MHz, CDCl$_3$): δ 8.63, 8.58, and 8.55 (3s, 1H, Ar—H), 8.13 (m, 1H, Ar—H), 7.57-7.43 (m, 3H, Ar—H), 6.16 and 6.05 (2d, 1H, H-1', J=4.9, 3.9 Hz, respectively), 4.58, 4.54, and 4.47 (3t, 1H, H-2', J=4.4, 4.2, 4.2 Hz, respectively), 4.35-4.31 (m, 1H, H-3'), 4.19-4.15 (m, 1H, H-4'), 4.08-4.02 (m, 1H, H-5'), 3.83-3.79 (m, 1H, H-5'), 0.972, 0.969, 0.96, 0.93, 0.925, 0.85, 0.84, and 0.81 (8s, 27H, t-Bu), 0.17, 0.16, 0.15, 0.10, 0.09, 0.02, 0.01, −0.008, −0.12, and −0.17 (10s, 18H, SiCH$_3$). $^{13}$C NMR (125 MHz, CDCl$_3$): δ 159.81, 159.22, 155.97, 155.60, 155.10, 154.06, 152.81, 151.63, 144.62, 144.09, 143.72, 143.64, 143.57, 129.21, 129.12, 129.03, 128.94, 128.91, 125.14, 125.06, 125.03, 120.84, 120.10, 119.22, 117.19, 108.86, 108.77, 108.72, 89.61, 89.06, 88.99, 85.70, 85.56, 85.39, 76.66, 76.61, 76.46, 71.76, 71.47, 71.42, 62.45, 62.28, 62.19, 26.33, 26.31, 26.02, 25.86, 18.78, 18.75, 18.27, 18.09, 18.07, −4.09, −4.12, −4.15, −4.45, −4.49, −4.53, −4.57, −4.59, −4.72, −5.11, −5.19, −5.23. HRMS calculated for C$_{34}$H$_{57}$N$_{10}$O$_5$Si$_3$ [M+H]$^+$ 769.3816. found 769.3839.

Example 40

Biological Assay Protocol

The cytostatic effects of the test compounds on murine leukemia cells (L1210), human T-lymphocyte cells (CEM) and human cervix carcinoma cells (HeLa) were evaluated as follows: an appropriate number of cells suspended in growth medium were allowed to proliferate in 200-μL-wells of 96-well-microtiter plates in the presence of variable amounts of test compounds at 37° C. in a humidified CO$_2$-controlled atmosphere. After 48 h (L1210), 72 h (CEM) or 96 h (HeLa), the number of cells was counted in a Coulter counter. The IC$_{50}$ value is defined as the concentration required to inhibit cell proliferation by 50%.

The antiviral assays (except anti-human immunodeficiency virus (HIV) assays) were based on inhibition of virus-induced cytopathicity in HEL [herpes simplex virus type 1 (HSV-1), HSV-2 (G), vaccinia virus, and vesicular stomatitis virus, cytomegalovirus, and varicella-zoster virus], Vero (parainfluenza-3, reovirus-1, Coxsackie B4, and Punta Toro virus), HeLa (vesicular stomatitis virus, Coxsackie virus B4, and respiratory syncytial virus), MDCK (influenza A (H1N1; H3N2) and B virus) and CrFK (feline corona virus (FIPV) and feline herpes virus) cell cultures. Confluent cell cultures in microtiter 96-well plates were inoculated with 100 cell culture inhibitory dose-50 (CCID$_{50}$) of virus (1 CCID$_{50}$ being the virus dose to infect 50% of the cell cultures) in the presence of varying concentrations (100, 20, 4, 0.8 μg/mL) of the test compounds. Viral cytopathicity was recorded as soon as it reached completion in the control virus-infected cell cultures that were not treated with the test compounds.

The methodology of the anti-HIV assays was as follows: human CEM (~3×10$^5$ cells/mL) cells were infected with 100 CCID$_{50}$ of HIV(III$_B$) or HIV-2(ROD)/mL and seeded in 200 μL wells of a microtiter plate containing appropriate dilutions of the test compounds. After 4 days of incubation at 37° C., HIV-induced CEM giant cell formation was examined microscopically. The 50% effective concentration (EC$_{50}$) was defined as the compound concentration required to inhibit syncytia formation by 50%. The 50% cytostatic concentration (CC$_{50}$) was defined as the compound concentration required to inhibit CEM cell proliferation by 50% in comparison to mock-infected cell cultures.

Determination of GI$_{50}$s using ovarian cancer and colon carcinoma cell lines were essentially as described. See Lakshman, M. K.; Singh, M. K.; Parrish, D.; Balachandran, R.; Day, B. W. J. Org. Chem. 2010, 75, 2461-2473; Cui, Y.; Balachandran, R.; Day, B. W.; Floreancig, P. E. J. Org. Chem. 2012, 77, 2225-2235; Wan, S.; Wu, F.; Rech, J. C.; Green, M. E.; Balachandran, R.; Home, S. W.; Day, B. W.; Floreancig, P. E. J. Am. Chem. Soc. 2011, 133, 16668-16679; and Zhu, W.; Jimenez, M.; Jung, W. H.; Camarco, D. P.; Balachandran, R.; Vogt, A.; Day, B. W.; Curran, D. P. J. Am. Chem. Soc. 2010, 132, 9175-9187.

A 10 mM stock solution of paclitaxel (PTX), obtained from the Drug Synthesis Branch of the National Cancer Institute, was prepared in DMSO. Control samples contained 1% (v/v) DMSO vehicle, a level equivalent to that in the drug-treated cultures. Ovarian cancer cells were cultured in RPMI 1640 medium without phenol red containing 10% fetal bovine serum at 37° C. in a humidified 5% carbon dioxide incubator. 1A9/PTX10 and 1A9/PTX22 cells were maintained in the presence of 15 ng/mL PTX and 5 μg/mL verapamil. This medium was replaced with regular medium two to three days before plating the cells in 96 well plates. HCT116 and p53KO$^{-/-}$ cell lines were maintained in McCoy medium with 10% fetal bovine serum.

Cells were plated in 96-well tissue culture plates for 48 h and the compounds (prepared in 100% DMSO as a stock solution) were added in quadruplicate. At least five different concentrations were tested for each compound. In each experiment, one plate consisted entirely of cells and medium used for time zero cell number determination, at the time/day of addition of compounds. After four days, 20 μL of Promega Cell Titer reagent was added into each well and plates were incubated in the tissue culture incubator. Approximately 2 h later, the plates were read using a plate reader at 490 nm minus 630 nm absorbance wavelengths. The data was then analyzed using an Excel Spreadsheet grid. Resulting average values ranging from <50 or >50 cell culture expansion for two or more concentrations were used to calculate the GI$_{50}$.

The invention claimed is:

1. A compound having Formula I,

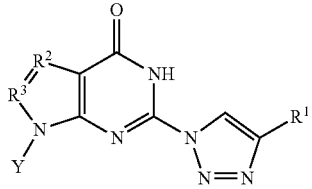

Formula I wherein:
$R^1$ represents an alkyl, an aryl, $-SiR^4$, $-SnR^5$, $-B(R^4)_2$, $-B(OH)_2$, an amide, an imide, or an organometallic;
$R^2$ and $R^3$ independently represent N, CH, or $CR^6$;
$R^4$ independently represents $-R^5$ or $-OR^5$;
$R^5$, $R^7$ and $R^8$, independently of each other and independently at each position, represent alkyl, cycloalkyl, or aryl;
$R^7$ and $R^8$ independently, may be combined to represent a heterocyclic alkyl or a heterocyclic aryl;
$R^6$ independently represents an alkyl or an aryl;
Y represents H, an alkyl, an aryl, or a saccharide moiety;
alkyl groups are branched or unbranched, saturated or unsaturated, and have 1-18 carbon atoms in their longest chain;
cycloalkyl groups are carbocyclic or heterocyclic, fused or unfused, non-aromatic ring systems having a total of 5-16 ring members including substituent rings;
aryl groups are carbocyclic or heterocyclic;
carbocyclic aryl groups are fused or unfused ring systems having a total of 6-16 ring members including substituent rings;
heterocyclic aryl groups are fused or unfused ring systems having a total of 5-16 ring members including substituent rings;
halo substituents are fluoro, chloro, bromo, or iodo;
each alkyl, cycloalkyl, and aryl, independently, may be unsubstituted or substituted with one or more substituent at any position;
alkyl substituents are halo, hydroxyl, $-OR^5$, $-SR^5$, $-S(O)R^4$, $-S(O)_2R^4$, $-NH_2$, $-NHR^5$, $-NR^7R^8$, cycloalkyl, or aryl;
cycloalkyl substituents are halo, hydroxyl, $-OR^5$, $-SR^5$, $-NH_2$, $-NHR^5$, $-NR^7R^8$, alkyl, cycloalkyl, or aryl;
aryl substituents are halo, hydroxyl, $-OR^5$, $-SR^5$, $-NH_2$, $-NHR^5$, $-NR^7R^8$, $-CN$, alkyl, cycloalkyl, aryl, nitro, or carboxyl; and
heterocyclic alkyl and heterocyclic aryl have at least one heteroatom selected from the group consisting of oxygen, nitrogen and sulfur.

2. A compound according to claim 1, wherein Y represents a saccharide moiety, and the saccharide moiety has the following structure:

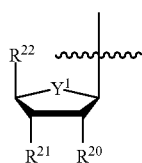

wherein:
$Y^1$ represents C, N, or O;
$R^{20}$ and $R^{21}$ independently represent H, $-OR^{23}$, $-NR^7R^8$, $R^6$, or halo;
$R^{22}$ represents H, OH, $-CH_2OR^6$, $-CH_2OR^{23}$, $-NR^7R^8$, $-CH_2NR^7R^8$, $R^6$; and
$R^{23}$ represents H or a protecting group.

3. A compound according to claim 2, wherein $Y^1$ represents O.

4. A compound according to claim 2, wherein $R^{22}$ represents $-CH_2O(alkyl)$ or $-CH_2OR^{23}$.

5. A compound according to claim 1, wherein the saccharide moiety is selected from the group consisting of 1-ribosyl and 2'-deoxy-1-ribosyl.

6. A compound according to claim 1, wherein $R^1$ is an imide and the imide is represented by:

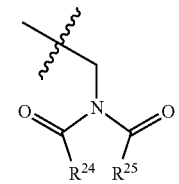

wherein:
$R^{24}$ and $R^{25}$ are independently an alkyl or an aryl; and
$R^{24}$ and $R^{25}$ independently, may be combined to represent a succinimidyl group that may be fused or unfused, and substituted or unsubstituted.

7. A compound according to claim 6, wherein $R^1$ is phthalimidyl.

8. A compound according to claim 1, wherein $R^1$ is an amide and the amide is represented by:

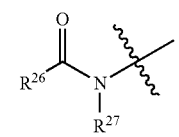

wherein:
$R^{26}$ and $R^{27}$ are independently an alkyl or an aryl.

9. A compound according to claim 1, wherein $R^1$ is an organometallic and the organometallic has a complex of Fe, Mo, Ru, or Pt.

10. A compound according to claim 9, wherein $R^1$ is ferrocenyl.

11. A compound according to claim 1, wherein Y represents a saccharide moiety selected from the group consisting of 1-ribosyl and 2'-deoxy-1-ribosyl; $R^2$ is N; $R^3$ is CH; and $R^1$ represents:

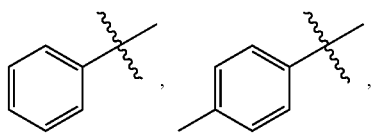

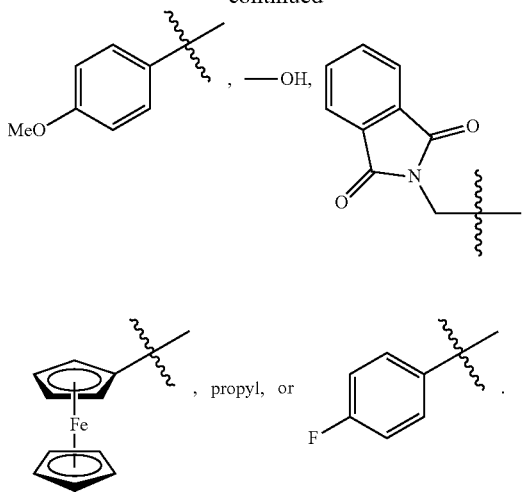

12. A compound having Formula II,

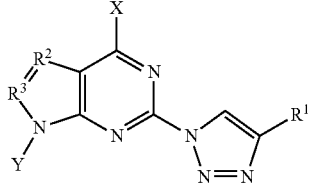

Formula II wherein:
R¹ represents an alkyl, an aryl, —SiR⁴, —SnR⁵, —B(R⁴)₂, —B(OH)₂, an amide, an imide, or an organometallic;
R² and R³ independently represent N, CH, or CR⁶;
X represents —OR⁹, —SR⁹, or —NR⁹R¹⁰;
Y represents H, an alkyl, an aryl, or a saccharide moiety;
R⁴ independently represents —R⁵ or —OR⁵;
R⁵, R⁷ and R⁸, independently of each other and independently at each position, represent alkyl, cycloalkyl, or aryl; and
R⁶ independently represents an alkyl or an aryl;
R⁹ and R¹⁰ independently represent H, an alkyl, or an aryl;
R⁷ and R⁸, R⁹ and R¹⁰ independently, may be combined to represent a heterocyclic alkyl or a heterocyclic aryl;
alkyl groups are branched or unbranched, saturated or unsaturated, and have 1-18 carbon atoms in their longest chain;
cycloalkyl groups are carbocyclic or heterocyclic, fused or unfused, non-aromatic ring systems having a total of 5-16 ring members including substituent rings;
aryl groups are carbocyclic or heterocyclic;
carbocyclic aryl groups are fused or unfused ring systems having a total of 6-16 ring members including substituent rings;
heterocyclic aryl groups are fused or unfused ring systems having a total of 5-16 ring members including substituent rings;
halo substituents are fluoro, chloro, bromo, or iodo;
each alkyl, cycloalkyl, and aryl, independently, may be unsubstituted or substituted with one or more substituent at any position;
alkyl substituents are halo, hydroxyl, —OR⁵, —SR⁵, —S(O)R⁴, —S(O)₂R⁴, —NH₂, —NHR⁵, —NR⁷R⁸, cycloalkyl, or aryl;
cycloalkyl substituents are halo, hydroxyl, —OR⁵, —SR⁵, —NH₂, —NHR⁵, —NR⁷R⁸, alkyl, cycloalkyl, or aryl;
aryl substituents are halo, hydroxyl, —OR⁵, —SR⁵, —NH₂, —NHR⁵, —NR⁷R⁸, —CN, alkyl, cycloalkyl, aryl, nitro, or carboxyl; and
heterocyclic alkyl and heterocyclic aryl have at least one heteroatom selected from the group consisting of oxygen, nitrogen and sulfur.

13. A compound according to claim 12, wherein X is —NR⁹R¹⁰ and R¹ represents —SiR⁴, —SnR⁵, —B(R⁴)₂, —B(OH)₂, an imide, or an organometallic.

14. A compound according to claim 12, wherein X is —NR⁹R¹⁰ and R⁹ and R¹⁰ independently represent an alkyl or an aryl.

15. A compound according to claim 12, wherein R² is N and R³ is CH.

16. A compound according to claim 12, wherein R¹ is phenyl.

17. A compound according to claim 12, wherein R⁹ and R¹⁰ independently represent H or CH₂Ph; or R⁹ and R¹⁰ are combined to represent CH₂CH₂OCH₂CH₂.

18. A compound according to claim 12, wherein R¹ is an imide and the imide is represented by:

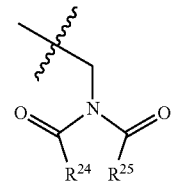

wherein:
R²⁴ and R²⁵ are independently an alkyl or an aryl; and
R²⁴ and R²⁵ independently, may be combined to represent a succinimidyl group that may be fused or unfused, and substituted or unsubstituted.

19. A compound according to claim 18, wherein R¹ is phthalimidyl.

20. A compound according to claim 12, wherein R¹ is an amide and the amide is represented by:

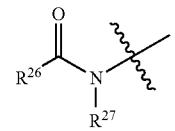

wherein:
R²⁶ and R²⁷ are independently an alkyl or an aryl.

21. A compound according to claim 12, wherein R¹ is an organometallic and the organometallic has a complex of Fe, Mo, Ru, or Pt.

22. A compound according to claim 21, wherein R¹ is ferrocenyl.

23. A compound according to claim 12, wherein Y represents a saccharide moiety, and the saccharide moiety has the following structure:

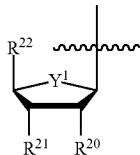

wherein:
$Y^1$ represents C, N, or O;
$R^{20}$ and $R^{21}$ independently represent H, —$OR^{23}$, —$NR^7R^8$, $R^6$, or halo;
$R^{22}$ represents H, OH, —$CH_2OR^6$, —$CH_2OR^{23}$, —$NR^7R^8$, —$CH_2NR^7R^8$, $R^6$; and
$R^{23}$ represents H or a protecting group.

24. A compound according to claim 23, wherein $Y^1$ represents O.

25. A compound according to claim 23, wherein $R^{22}$ represents —$CH_2O$(alkyl) or —$CH_2OR^{23}$.

26. A compound according to claim 12, wherein the saccharide moiety is selected from the group consisting of 1-ribosyl and 2'-deoxy-1-ribosyl.

27. A compound having Formula III,

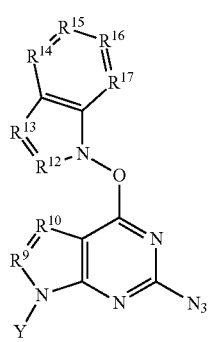

Formula III wherein:
$R^9$, $R^{10}$, $R^{12}$, $R^{13}$, $R^{14}$, $R^{15}$, $R^{16}$, and $R^{17}$ independently represent N or $CR^{11}$;
$R^{11}$ independently represents —$R^{18}$, —$OR^{19}$, —$SR^{19}$, —$N(R^{18})_2$, $R^{18}C(O)$—, nitro, or halo;
$R^{18}$ independently represents H, an alkyl group, or an aryl;
$R^{19}$ independently represents $R^{18}$ or a protecting group;
Y represents $R^{18}$ or a saccharide moiety;
alkyl groups are branched or unbranched, saturated or unsaturated, and have 1-18 carbon atoms in their longest chain;
cycloalkyl groups are carbocyclic or heterocyclic, fused or unfused, non-aromatic ring systems having a total of 5-16 ring members including substituent rings;
aryl groups are carbocyclic or heterocyclic;
carbocyclic aryl groups are fused or unfused ring systems having a total of 6-16 ring members including substituent rings;
heterocyclic aryl groups are fused or unfused ring systems having a total of 5-16 ring members including substituent rings;
halo substituents are fluoro, chloro, bromo, or iodo;
each alkyl, cycloalkyl, and aryl, independently, may be unsubstituted or substituted with one or more substituent at any position;
alkyl substituents are halo, hydroxyl, —$OR^5$, —$SR^5$, —$S(O)R^4$, —$S(O)_2R^4$, —$NH_2$, —$NHR^5$, —$NR^7R^8$, cycloalkyl, or aryl;
cycloalkyl substituents are halo, hydroxyl, —$OR^5$, —$SR^5$, —$NH_2$, —$NHR^5$, —$NR^7R^8$, alkyl, cycloalkyl, or aryl;
aryl substituents are halo, hydroxyl, —$OR^5$, —$SR^5$, —$NH_2$, —$NHR^5$, —$NR^7R^8$, —CN, alkyl, cycloalkyl, aryl, nitro, or carboxyl; and
heterocyclic alkyl and heterocyclic aryl have at least one heteroatom selected from the group consisting of oxygen, nitrogen and sulfur;
$R^4$ independently represents —$R^5$ or —$OR^5$;
$R^5$, $R^7$ and $R^8$, independently of each other and independently at each position, represent alkyl, cycloalkyl, or aryl; and
$R^7$ and $R^8$ independently, may be combined to represent a heterocyclic alkyl or a heterocyclic aryl.

28. A compound according to claim 27, wherein Y represents a saccharide moiety, and the saccharide moiety has the following structure:

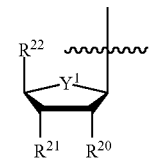

wherein:
$Y^1$ represents C, N, or O;
$R^{20}$ and $R^{21}$ independently represent H, —$OR^{23}$, —$NR^7R^8$, $R^6$, or halo;
$R^{22}$ represents H, OH, —$CH_2OR^6$, —$CH_2OR^{23}$, —$NR^7R^8$, —$CH_2NR^7R^8$, $R^6$;
$R^{23}$ represents H or a protecting group; and
$R^6$ represents an alkyl or an aryl.

29. A compound according to claim 28, wherein $Y^1$ represents O.

30. A compound according to claim 28, wherein $R^{22}$ represents —$CH_2O$(alkyl) or —$CH_2OR^{23}$.

31. A compound according to claim 27, wherein the saccharide moiety is selected from the group consisting of 1-ribosyl and 2'-deoxy-1-ribosyl.

32. A compound according to claim 27, wherein no more than one of $R^{14}$, $R^{15}$, $R^{16}$, and $R^{17}$ represent N.

33. A compound according to claim 27, wherein $R^9$, $R^{14}$, $R^{15}$, $R^{16}$, and $R^{17}$ are CH; and $R^{10}$, $R^{12}$, and $R^{13}$ are N.

34. A compound according to claim 27, wherein $R^9$, $R^{14}$, $R^{15}$, and $R^{16}$ are CH; $R^{10}$, $R^{12}$, and $R^{13}$ are N; and $R^{17}$ is N or CH.

35. A method of treating cancer, comprising administering to a patient in need thereof an effective amount of a compound of Formula I or a compound below:
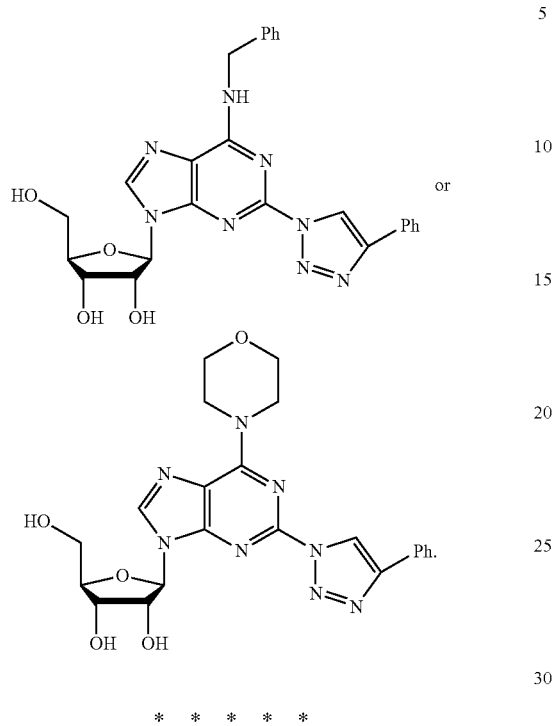
* * * * *